US 6,740,118 B2

(12) United States Patent
Eisermann et al.

(10) Patent No.: US 6,740,118 B2
(45) Date of Patent: May 25, 2004

(54) INTERVERTEBRAL PROSTHETIC JOINT

(75) Inventors: Lukas Eisermann, Memphis, TN (US); Eddie F. Ray, III, Collierville, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 237 days.

(21) Appl. No.: 10/042,589

(22) Filed: Jan. 9, 2002

(65) Prior Publication Data

US 2003/0208273 A1 Nov. 6, 2003

(51) Int. Cl.⁷ .................................................. A61F 2/44
(52) U.S. Cl. .................................................... 623/17.14
(58) Field of Search ........................... 623/17.11, 17.13, 623/17.14, 17.15, 17.16; 606/61

(56) References Cited

U.S. PATENT DOCUMENTS

| | | | |
|---|---|---|---|
| 4,759,766 A | 7/1988 | Buettner-Janz et al. | |
| 5,258,031 A | 11/1993 | Salib et al. | |
| 5,314,477 A | 5/1994 | Marnay | |
| 5,401,269 A | 3/1995 | Buttner-Janz et al. | |
| 5,425,773 A | 6/1995 | Boyd et al. | |
| 5,562,738 A | 10/1996 | Boyd et al. | |
| 5,665,122 A * | 9/1997 | Kambin .................... | 623/17.16 |
| 5,676,701 A | 10/1997 | Yuan et al. | |
| 5,683,465 A * | 11/1997 | Shinn et al. ............. | 623/17.14 |
| 5,782,832 A * | 7/1998 | Larsen et al. ................ | 606/61 |
| 5,895,428 A | 4/1999 | Berry | |
| 5,899,941 A * | 5/1999 | Nishijima et al. ........ | 623/17.15 |
| 5,989,291 A | 11/1999 | Ralph et al. | |
| 6,019,792 A | 2/2000 | Cauthen | |
| 6,063,121 A * | 5/2000 | Xavier et al. ............. | 623/17.15 |
| 6,113,637 A | 9/2000 | Gill et al. | |
| 6,156,067 A | 12/2000 | Bryan et al. | |
| 6,179,874 B1 | 1/2001 | Cauthen | |
| 6,368,350 B1 * | 4/2002 | Erickson et al. ......... | 623/17.14 |
| 6,517,580 B1 * | 2/2003 | Ramadan et al. ........ | 623/17.15 |
| 6,572,653 B1 * | 6/2003 | Simonson ................ | 623/17.13 |

FOREIGN PATENT DOCUMENTS

| | | |
|---|---|---|
| FR | 2 718 635 | 4/1994 |
| WO | WO 93/10725 | 6/1993 |

* cited by examiner

Primary Examiner—Eduardo C. Robert
(74) Attorney, Agent, or Firm—Woodard, Emhardt, Moriarty, McNett & Henry LLP

(57) ABSTRACT

An intervertebral prosthetic joint including a first articular component adapted to engage a first vertebra and a second articular component adapted to engage a second vertebra. The articular components include abutting convex and concave articular surfaces that cooperate to permit articulating motion between the articular components. At least one of the convex and concave articular surfaces includes at least one surface depression that is configured to facilitate removal of matter disposed between abutting portions of the articular surfaces. In one embodiment of the prosthetic joint, each of the articular components has a vertebral bearing surface and a flange extending therefrom that is configured to penetrate a corresponding one of the first and second vertebrae, with the flange defining at least one opening extending therethrough to permit bone through-growth.

40 Claims, 6 Drawing Sheets

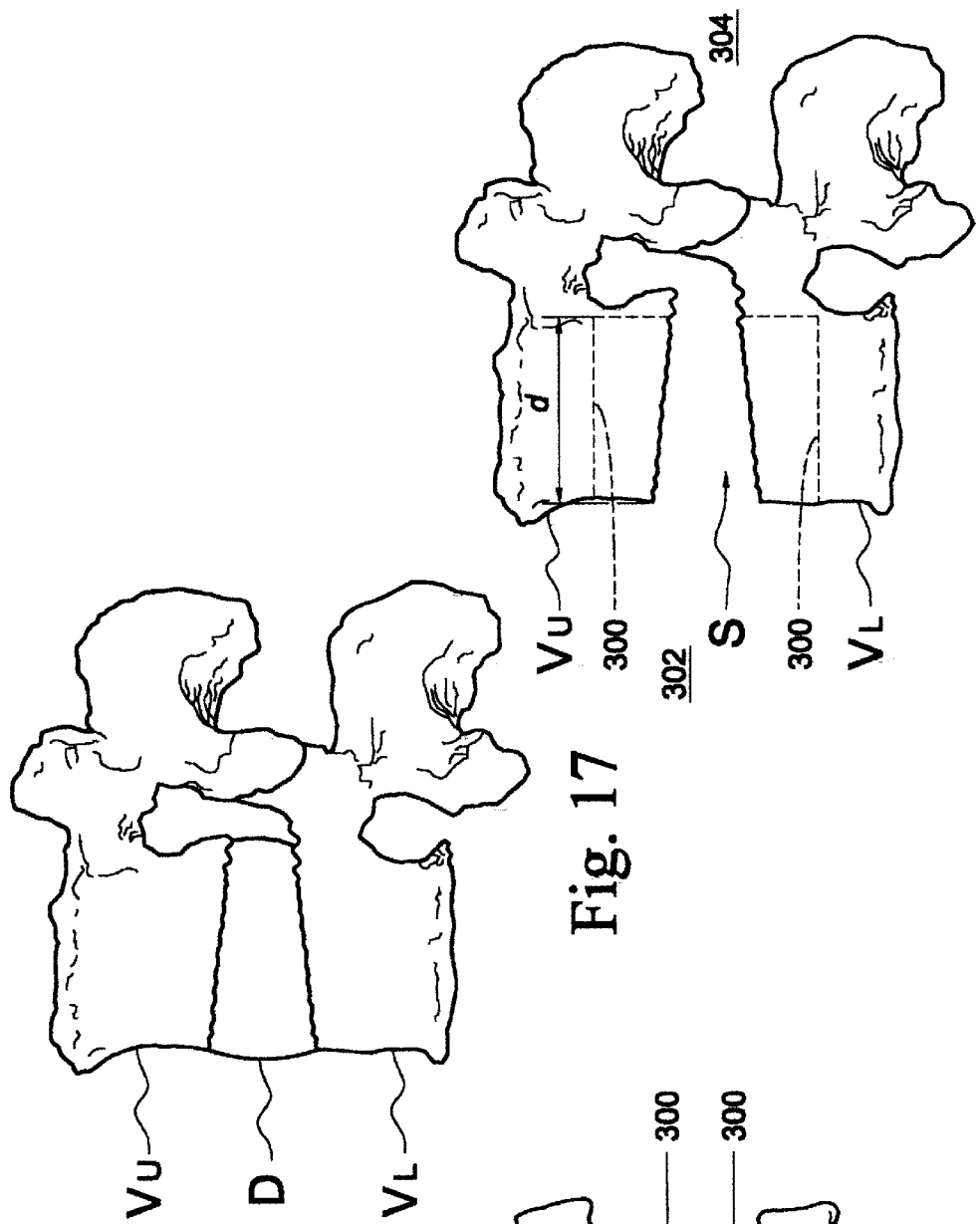
Fig. 17
Fig. 19
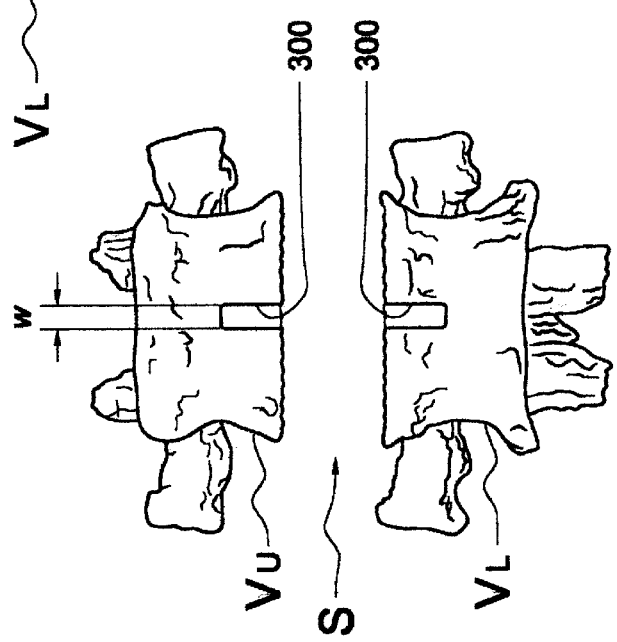
Fig. 18

INTERVERTEBRAL PROSTHETIC JOINT

FIELD OF THE INVENTION

The present invention relates generally to the field of spinal implants, and more particularly relates to an intervertebral prosthetic joint for use in the total or partial replacement of a natural intervertebral disc.

BACKGROUND OF THE INVENTION

In the treatment of diseases, injuries or malformations affecting spinal motion segments, and especially those affecting disc tissue, it has long been known to remove some or all of a degenerated, ruptured or otherwise failing disc. In cases involving intervertebral disc tissue that has been removed or is otherwise absent from a spinal motion segment, corrective measures are indicated to insure the proper spacing of the vertebrae formerly separated by the removed disc tissue.

In some instances, the two adjacent vertebrae are fused together using transplanted bone tissue, an artificial fusion component, or other compositions or devices. Spinal fusion procedures, however, have raised concerns in the medical community that the bio-mechanical rigidity of intervertebral fusion may predispose neighboring spinal motion segments to rapid deterioration. More specifically, unlike a natural intervertebral disc, spinal fusion prevents the fused vertebrae from pivoting and rotating with respect to one another. Such lack of mobility tends to increase stresses on adjacent spinal motion segments. Additionally, several conditions may develop within adjacent spinal motion segments, including disc degeneration, disc herniation, instability, spinal stenosis, spondylosis and facet joint arthritis. Consequently, many patients may require additional disc removal and/or another type of surgical procedure as a result of spinal fusion. Alternatives to spinal fusion are therefore desirable.

Several different types of intervertebral disc arthroplasty devices have been proposed for preventing the collapse of the intervertebral space between adjacent vertebrae while maintaining a certain degree of stability and range of pivotal and rotational motion therebetween. Such devices typically include two or more articular elements that are attached to respective upper and lower vertebrae. The articular elements are anchored to the upper and lower vertebrae by a number of methods, including the use of bone screws that pass through corresponding openings in each of the elements and thread into vertebral bone, and/or by the inclusion of spikes or teeth that penetrate the vertebral endplates to inhibit migration or expulsion of the device. The articular elements are typically configured to allow the elements, and correspondingly the adjacent vertebrae, to pivot and/or rotate relative to one another.

As discussed above, prior intervertebral disc arthroplasty devices are relatively difficult to implant between adjacent vertebrae. To implant such devices, the adjacent vertebrae are spread apart a distance that is somewhat greater than the normal distance separating the vertebrae so that the device can be maneuvered between the vertebrae and the anchors can be engaged to the vertebral endplates. Such an operation presents a risk of injury to the vertebrae caused by misplacement and/or scratching of the vertebral endplates or other tissue by the anchors. Such operation also presents a risk of injury resulting from over-distraction of the intervertebral space. As also discussed above, other types of prior arthroplasty devices require the threading of bone screws or another type of fastener into the adjacent vertebrae. However, this type of anchoring method requires precise placement and orientation of the bone screws to provide adequate anchoring and to avoid injury to adjacent tissue or vertebral structures. Moreover, prior arthroplasty devices are prone to increased wear or possible malfunctioning if debris or particulate matter becomes lodged between the articular elements.

Thus, there is a general need in the industry to provide an improved intervertebral prosthetic joint. The present invention satisfies this need and provides other benefits and advantages in a novel and unobvious manner.

SUMMARY OF THE INVENTION

The present invention relates generally to an intervertebral prosthetic joint. While the actual nature of the invention covered herein can only be determined with reference to the claims appended hereto, certain forms of the invention that are characteristic of the preferred embodiments disclosed herein are described briefly as follows.

One form of the present invention is directed to an intervertebral prosthetic joint, comprising a first component adapted to engage a first vertebra and including a first articular surface, and a second component adapted to engage a second vertebra and including a second articular surface, with the first and second articular surfaces cooperating to permit articulating motion between the first and second components, and with at least one of the first and second articular surfaces including at least one surface depression configured to facilitate removal of matter disposed therebetween.

Another form of the present invention is directed to an intervertebral prosthetic joint, comprising a first articular component adapted to engage a first vertebra and including a projection, and a second articular component adapted to engage a second vertebra and including a recess, with at least a portion of the projection being disposed within the recess to permit articulating motion between the first and second components, and with at least one of the projection and the recess defining at least one passage configured to facilitate removal of matter disposed therebetween.

Another form of the present invention is directed to an intervertebral prosthetic joint, comprising a first articular component having a bearing surface adapted to engage a first vertebra, and a second articular component having a bearing surface adapted to engage a second vertebra, with each of the first and second articular components including a flange extending from the bearing surface and adapted to penetrate a corresponding one of the first and second vertebrae, and wherein the flange defines at least one opening extending therethrough to permit bone through-growth.

It is one object of the present invention to provide an improved intervertebral prosthetic joint. Further objects, features, advantages, benefits, and aspects of the present invention will become apparent from the drawings and description contained herein.

BRIEF DESCRIPTION OF THE DRAWINGS

FIG. 17 is a lateral view of a portion of the spinal column, illustrating a pair of adjacent upper and lower vertebrae separated by a natural intervertebral disc.

FIG. 18 is an anterior view of the portion of the spinal column shown in FIG. 17, illustrating the removal of portions of the upper and lower vertebrae to accommodate insertion of the intervertebral prosthetic joint illustrated in FIG. 1 therebetween.

FIG. 19 is a lateral view of the portion of the spinal column shown in FIG. 18.

DESCRIPTION OF THE PREFERRED EMBODIMENTS

Figure 1:
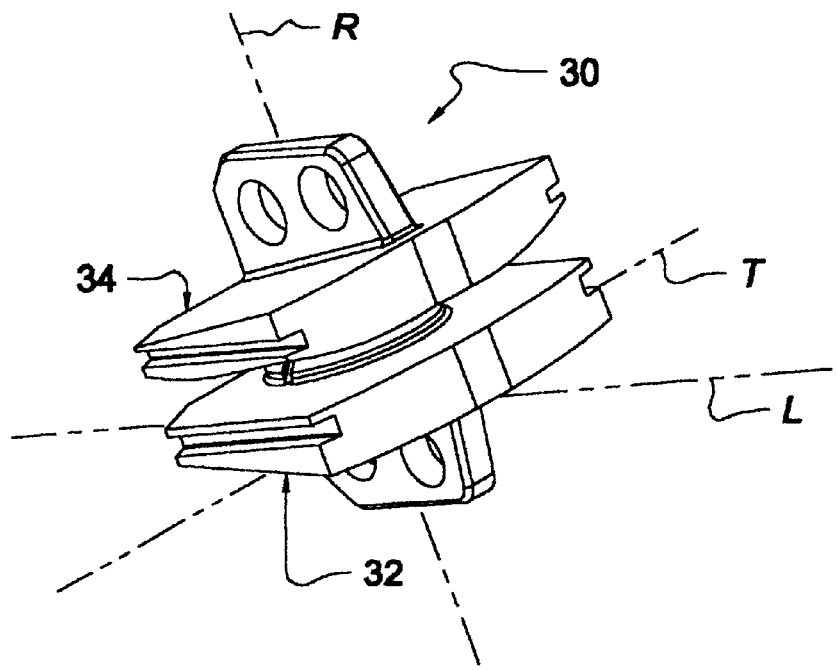
FIG. 1 is a perspective view of an intervertebral prosthetic joint according to one form of the present invention.

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Figure 2:
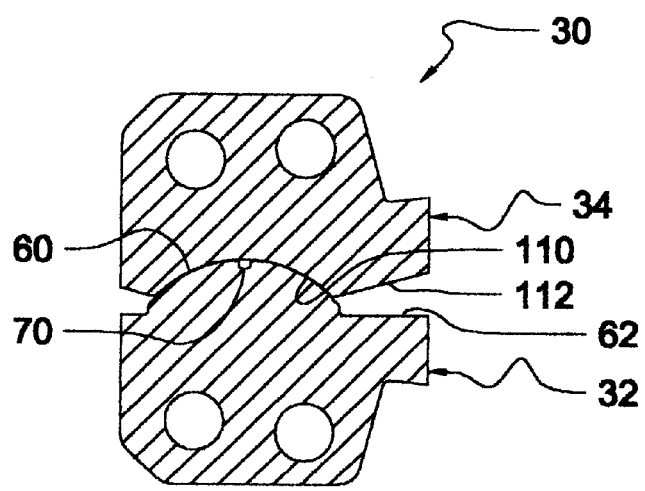
FIG. 2 is a sectional view of the intervertebral prosthetic joint illustrated in FIG. 1.
Figure 8:
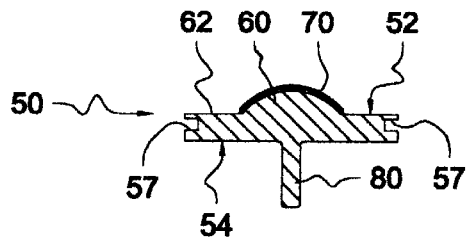
FIG. 8 is a sectional view of the ball component illustrated in FIG. 5, taken along line 8—8 of FIG. 5.
Figure 5:
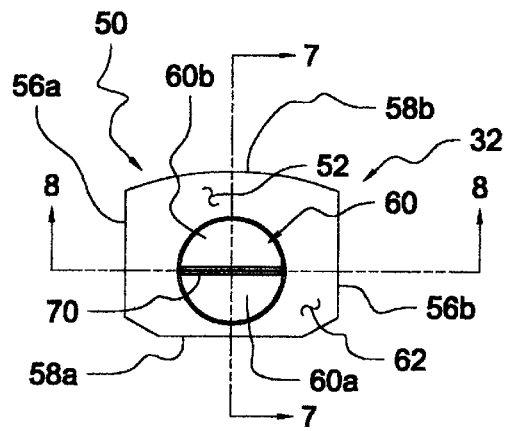
FIG. 5 is a top view of the ball component illustrated in FIG. 3.
Figure 7:
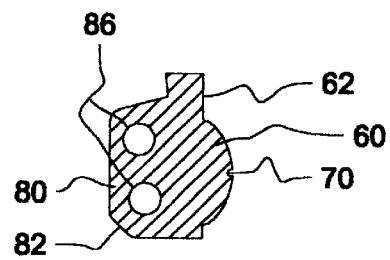
FIG. 7 is a sectional view of the ball component illustrated in FIG. 5, taken along line 7—7 of FIG. 5.
Figure 3:
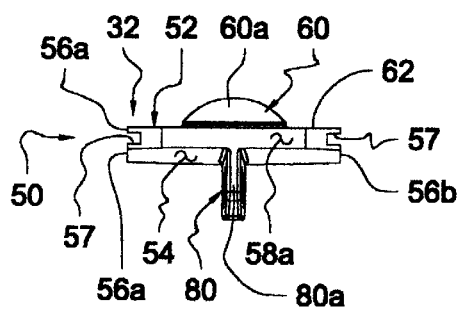
FIG. 3 is a front view of a ball component according to one embodiment of the present invention for use with the intervertebral prosthetic joint illustrated in FIG. 1.
Figure 4:
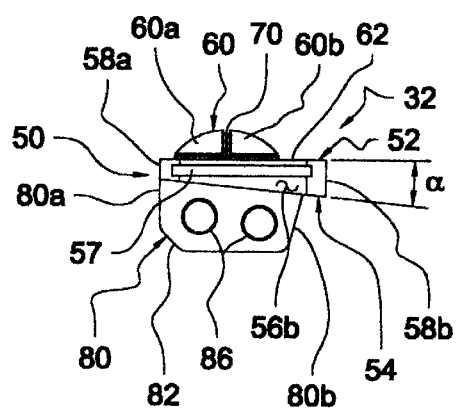
FIG. 4 is a side view of the ball component illustrated in FIG. 3.

Referring to FIGS. 1–2, shown therein is an intervertebral prosthetic joint 30 according to one form of the present invention. The articulating joint 30 extends generally along a longitudinal axis L and includes a first articular component 32 and a second articular component 34. The articular components 32, 34 cooperate to form the articulating joint 30 which is sized and configured for disposition within an intervertebral space between adjacent vertebral bodies.

The articulating joint 30 provides relative pivotal and rotational movement between the adjacent vertebral bodies to maintain or restore motion substantially similar to the normal bio-mechanical motion provided by a natural intervertebral disc. More specifically, the articular components 32, 34 are permitted to pivot relative to one another about a number of axes, including lateral or side-to-side pivotal movement about longitudinal axis L and anterior-posterior pivotal movement about a transverse axis T. It should be understood that in a preferred embodiment of the invention, the articular components 32, 34 are permitted to pivot relative to one another about any axes that lies in a plane that intersects longitudinal axis L and transverse axis T. Additionally, the articular components 32, 34 are preferably permitted to rotate relative to one another about a rotational axis R. Although the articulating joint 30 has been illustrated and described as providing a specific combination of articulating motion, it should be understood that other combinations of articulating movement are also possible and are contemplated as falling within the scope of the present invention. It should also be understood that other types of articulating movement are also contemplated, such as, for example, relative translational or linear motion.

Although the articular components 32, 34 of prosthetic joint 30 may be formed from a wide variety of materials, in one embodiment of the invention, the articular components 32, 34 are formed of a cobalt-chrome-molybdenum metallic alloy (ASTM F799 or F-75). However, in alternative embodiments of the invention, the articular components 32, 34 may be formed of other metallic materials such as titanium or stainless steel, a polymeric material such as polyethylene, or any other biocompatible material that would be apparent to one of ordinary skill in the art. The surfaces of the articular components 32, 34 that are positioned in direct contact with vertebral bone are preferably coated with a bone-growth promoting substance, such as, for example, a hydroxyapatite coating formed of calcium phosphate. Additionally, the surface of the articular components 32, 34 that are positioned in direct contact with vertebral bone are preferably roughened prior to being coated with the bone-growth promoting substance to further enhance bone on-growth. Such surface roughening may be accomplished by way of, for example, acid etching, knurling, application of a bead coating, or other methods of roughening that would occur to one of ordinary skill in the art.

Referring to FIGS. 3–8, shown therein are various details regarding the articular component 32. Articular component 32 includes a support plate 50 having an articular surface 52 and an opposite bearing surface 54. Support plate 50 is preferably sized and shaped to substantially correspond to the size and shape of the vertebral endplate of an adjacent vertebra. The articular surface 52 and the bearing surface 54 are separated by a pair of laterally facing surfaces 56a, 56b and a pair of axially facing surfaces 58a, 58b. The laterally facing surfaces 56a, 56b each preferably define a channel 57 extending along at least a portion of the length of the support plate 50. The channels 57 are configured to engage a corresponding portion of a surgical instrument (not shown) to aid in the manipulation and insertion of the prosthetic joint 30 within an intervertebral space between adjacent vertebrae. The surgical instrument (not shown) is preferably configured to hold the articular components 32, 34 at a predetermined orientation and spatial relationship relative to one another during manipulation and insertion of the prosthetic joint 30, and to release the articular components 32, 34 once properly positioned between the adjacent vertebrae.

In a preferred embodiment of the invention, the articular surface 52 includes a projection 60 surrounded by a substantially planar surface 62. In one embodiment of the invention, the projection 60 has a convex shape and is preferably configured as a spherical-shaped ball. In another embodiment of the invention, the spherical-shaped surface of the projection has a large enough radius of curvature such that the axis about which the articular components 32, 34 pivot relative to one another is located at or below the planar surface 62 (i.e., the center of curvature is located at or below planar surface 62). However, it should be understood that the pivot axis may alternatively be positioned above the planar surface 62. It should also be understood that other configurations of the projection 60 are also contemplated, such as, for example, cylindrical, elliptical or other arcuate configurations or possibly non-arcuate configurations. It should also be understood that the planar surface 62 may take on non-planar configurations, such as, for example, an angular or conical configuration extending about the projection 60.

In a preferred embodiment of the invention, the convex articular surface of the projection 60 is interrupted by a surface depression or cavity 70 extending along the projection 60. In one embodiment of the invention, the surface depression 70 is configured as a groove. However, as will be discussed in further detail below, it should be understood that other types of surface depressions are also contemplated. One purpose of the groove 70 is to facilitate the removal of matter disposed between abutting portions of the articular components 32, 34. More specifically, the groove 70 provides a means for clearing out matter such as, for example, particulate material, that is disposed between the abutting articular surfaces of components 32, 34.

Figure 14:
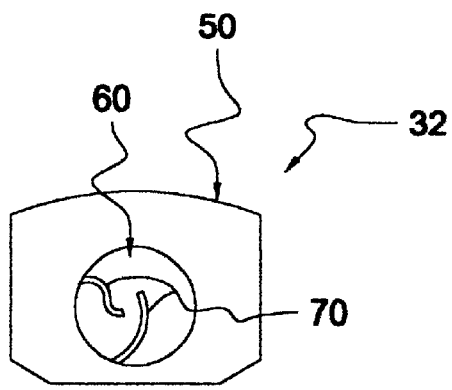
FIG. 14 is a top view of a ball component according to another embodiment of the present invention.

In one embodiment of the invention, the groove 70 extends along the convex surface of the spherical-shaped ball 60 in such a manner as to divide the ball 60 into two substantially symmetrical portions 60a, 60b, with each portion extending about approximately 180° of the overall circumference or periphery of the ball 60. However, it should be understood that the groove 70 may take on other configurations as well. For example, the groove 70 need not necessarily uniformly divide the ball 60 into symmetrical halves, but may alternatively be positioned at other locations along ball 60 and arranged at other angular orientations relative to ball 60. It should further be understood that the groove 70 need not necessarily extend entirely across the ball 60, but may alternatively extend across only a portion of the ball 60. For example, the groove 70 may extend across the ball 60 in such a manner that only a portion of the groove 70 extends beyond abutting portions of the articular components 32, 34 at some point during the articulating motion of joint 30. Additionally, it should be understood that the groove 70 need not necessarily have a linear configuration, but may alternatively take on angular configurations or non-linear configurations, such as, for example, the curvilinear configuration illustrated in FIG. 14. It should also be understood that any number of grooves 70 may be defined along the periphery of the ball 60, such as two or more grooves 70 arranged in a uniform manner or alternatively in a random or semi-random pattern, as also illustrated in FIG. 14. In one specific embodiment of the invention, the groove 70 is approximately 0.75 mm deep and approximately 0.4 mm wide and has a radiused bottom surface. However, it should be understood that other sizes and configurations of the groove 70 are contemplated as falling within the scope of the present invention.

In one embodiment of the invention, the bearing surface 54 is substantially planar and is oriented at an angle $\alpha$ relative to the planar surface 62 to define an outward taper extending from axial surface 58a toward axial surface 58b. In one embodiment, angle $\alpha$ falls within a range of 0 degrees to about 10 degrees. In a specific embodiment, angle $\alpha$ is about 3 degrees. In another specific embodiment, angle $\alpha$ is about 6 degrees. However, it should be understood that angle $\alpha$ may take on other values that correspond to the particular lordotic angle or morphology of the portion of the spinal column in which the prosthetic joint 30 is used. It should further be understood that the bearing surface 54 may be configured to accommodate spinal abnormalities such as scoliosis. In such case, the bearing surface 54 may be angled relative to the planar surface 62 to define a taper extending between the lateral surfaces 56a, 56b. It should also be understood that the bearing surface 54 may take on alternative configurations, such as, for example, a curved or arcuate configuration that corresponds to the particular contour of the adjacent vertebral endplate against which surface 54 abuts. It should likewise be understood that bearing surface 54 may be roughened and/or may define a number of surface projections to aid in gripping the vertebral endplate and to inhibit migration of the prosthetic joint 30 relative to the adjacent vertebra.

A flange member or keel 80 extends from the bearing surface 54 and is configured for disposition within a preformed opening in the adjacent vertebral endplate. In one embodiment, the keel 80 extends perpendicularly from the bearing surface 54 and is approximately centrally located along the bearing surface 54. However, it should be understood that other positions and orientations of the keel 80 are also contemplated. It should also be understood that the articular component 32 may include two or more keels 80 extending from the bearing surface 54.

Figure 6:
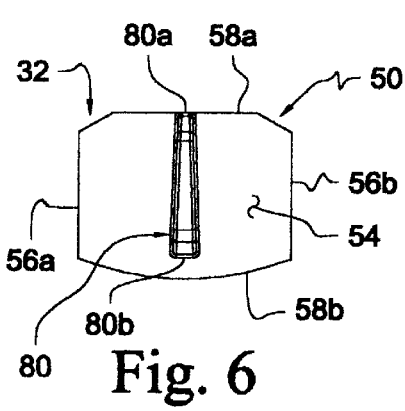
FIG. 6 is a bottom view of the ball component illustrated in FIG. 3.

The keel 80 extends from a location adjacent the axially facing surface 58a toward the axially facing surface 58b along a substantial portion of the support plate 50. Preferably, the keel 80 extends along substantially the entire length of the support plate 50. As illustrated in FIG. 6, the keel 80 is preferably wedge-shaped, defining an outward taper as the keel 80 extends from a leading or insertion end 80a towards a trailing end 80b. In one specific embodiment, the outward taper is about 4 degrees. However, other taper angles are also contemplated. It should also be understood that the keel 80 need not necessarily be tapered along it length. As will become apparent, the outward taper aids in the insertion of the keel 80 within preformed openings in the adjacent vertebrae. Additionally, the insertion end 80a of keel 80 includes a beveled surface 82 to further aid in the implantation of the prosthetic joint 30.

In another embodiment of the invention, the keel 80 may alternatively extend between the laterally facing surface 56a, 56b along a substantial portion of the support plate 50. Such an embodiment would accommodate insertion of the prosthetic joint 30 using a lateral approach as opposed to the anterior approach illustrated in FIGS. 20 and 21. In a further embodiment of the invention, the keel 80 may be tapered along its height, either tapering inwardly from bearing surface 54 to define a wedge shape or tapering outwardly from bearing surface 54 to define a dove-tail shape. In still another embodiment, the keel 80 may be configured as a winged keel, including a transverse portion extending across the main body portion of keel 80.

The keel 80 also includes a pair of openings 86 extending therethrough to facilitate bone through-growth to enhance fixation to the adjacent vertebra. However, it should be understood that any number of openings 86 may be defined through keel 80, including a single opening or three or more openings. It should also be understood that the openings 86 need not necessarily extend entirely through the keel 80, but may alternatively extend partially therethrough. It should further be understood that the keel 80 need not necessarily define any openings 86 extending either partially or entirely therethrough. Additionally, although the openings 86 are illustrated as having a circular configuration, it should be understood that other sizes and configures of openings 86 are also contemplated. As discussed above, the surfaces of the articular component 32 that are in direct contact with vertebral bone are preferably coated with a bone-growth promoting substance. Specifically, the bearing surface 54 and the surfaces of the keel 80 are preferably coated with hydroxyapatite to promote bony engagement with the adjacent vertebrae. As also discussed above, the bearing surface 54 and the surfaces of keel 80 are preferably roughened prior to application of the hydroxyapatite coating.

Referring to FIGS. 9–13, shown therein are various details regarding the articular component 34. Articular component 34 includes a support plate 100 having an articular surface 102 and an opposite bearing surface 104. Support plate 100 is preferably sized and shaped to substantially correspond to the size and shape of the vertebral endplate of an adjacent vertebra. The articular surface 102 and the bearing surface 104 are separated by a pair of laterally facing surfaces 106a, 106b and a pair of axially facing surfaces 108a, 108b. The laterally facing surfaces 106a, 106b each preferably define a channel 107 extending along at least a portion of the length of the support plate 100. Similar to channels 57 of articular element 32, channels 107 are configured to engage a corresponding portion of a surgical instrument (not shown) to aid in the manipulation and insertion of the prosthetic joint 30.

In a preferred embodiment of the invention, the articular surface 102 includes a recess 110 surrounded by a substantially conical surface 112. In one embodiment of the invention, the recess 110 has a concave shape, and is preferably configured as a spherical-shaped socket. However, it should be understood that other configurations of the recess 110 are also contemplated, such as, for example, cylindrical, elliptical or other arcuate configurations or possibly non-arcuate configurations. Conical surface 112 is tapered at an angle θ relative to a plane oriented parallel with the planar surface 52 of articular component 32 in such a manner as to define a uniform taper extending entirely about the concave recess 110. In this manner, relative pivotal motion between the articular components 32, 34 is limited to approximately +/- angle θ. In one embodiment, the angle θ falls within a range of about 10 degrees to about 20 degrees, thereby limiting the overall relative pivotal motion between the articular components 32, 34 within a range of just over 20 degrees to just over 40 degrees. In a specific embodiment, angle θ is about 16 degrees, thereby limiting the overall pivotal motion between the articular components 32, 34 to just over 32 degrees. As will become apparent, angle θ may take on other values that correspond to the desired amount of relative pivotal movement between the articular components 32, 34. It should also be understood that the conical surface 112 may take on other configurations, such as, for example, an angular configuration extending about the concave recess 110. It should also be understood that the surface 112 could alternatively be configured as a planar surface oriented parallel with the bearing surface 104, and that the surface 52 of articular component 32 could alternatively be configured as a conical or angled surface tapered at an angle θ, or that both of the surfaces 52, 112 could alternatively be configured as conical or angled surfaces tapered at a predetermined angle θ. In an embodiment where both of the surfaces 52, 112 are tapered at a predetermined angle θ, the angle θ is preferably about 8 degrees, thereby limiting the overall pivotal motion between the articular components 32, 34 to just over 32 degrees.

Although the concave recess 110 is illustrated as having a generally smooth, uninterrupted articular surface, it should be understood that a surface depression or cavity may be defined along a portion of the recess 110 to provide a means for clearing out matter, such as particulate debris, that is disposed between the abutting articular surfaces of components 32, 34. In such case, the convex articular surface of the ball 60 may alternatively define a generally smooth, uninterrupted articular surface. In another embodiment of the invention, each of the convex projection 60 and the concave recess 110 may define a surface depression to facilitate removal of particulate matter disposed between the abutting articular surfaces.

In one embodiment of the invention, the bearing surface 104 is substantially planar and is oriented at an angle α, similar to that of bearing surface 54 of articular component 32, to define an outward taper extending from axial surface 108a toward axial surface 108b. However, it should be understood that bearing surface 104 may take on alternative configurations, such as, for example, a curved or arcuate configuration that corresponds to the particular contour of the adjacent vertebral endplate against which surface 104 abuts. It should further be understood that the bearing surface 104 may be configured to accommodate spinal abnormalities such as scoliosis. In such case, the bearing surface 104 may be angled to define a taper extending between the lateral surfaces 106a, 106b. It should additionally be understood that the bearing surface 104 may be roughened and/or may define a number of surface projections to aid in gripping the vertebral endplate and to inhibit migration of the prosthetic joint 30 relative to the adjacent vertebra.

A flange member or keel 120, configured similar to the keel 80 of articular component 32, extends from the bearing surface 104. In one embodiment, the keel 120 extends perpendicularly from the bearing surface 104 and is approximately centrally located along bearing surface 104. However, it should be understood that other positions and orientations of the keel 120 are also contemplated. It should also be understood that the articular component 34 may include two or more keels 120 extending from the bearing surface 104.

Figure 11:
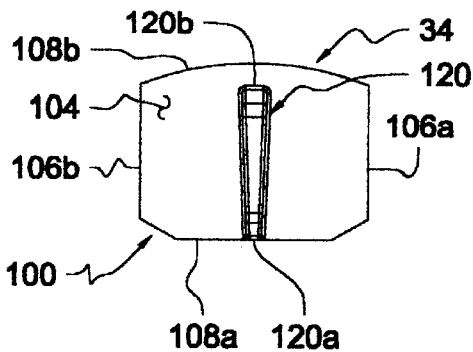
FIG. 11 is a top view of the socket component illustrated in FIG. 9.
Figure 10:
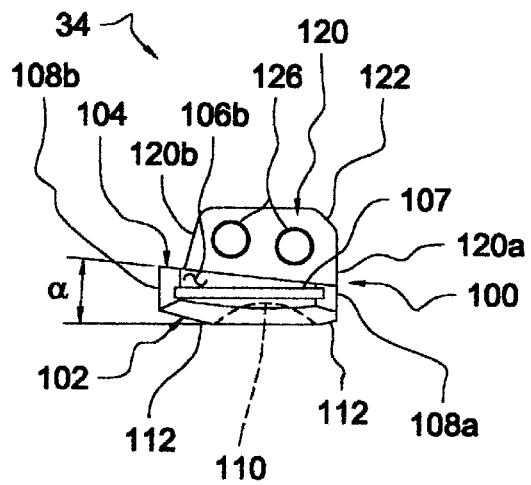
FIG. 10 is a side view of the socket component illustrated in FIG. 9.
Figure 9:
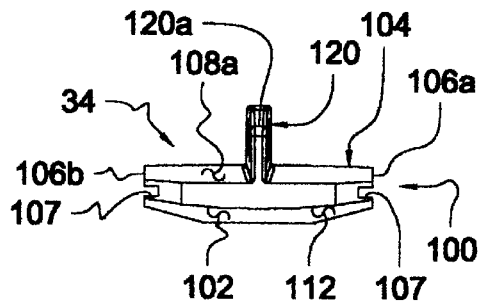
FIG. 9 is a front view of a socket component according to one embodiment of the present invention for use with the intervertebral prosthetic joint illustrated in FIG. 1.
Figure 13:
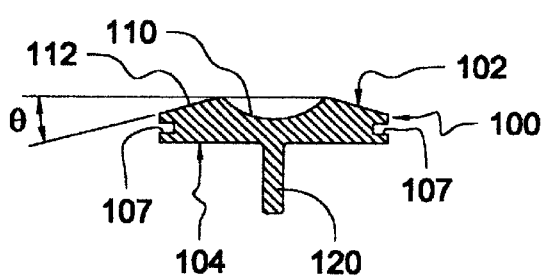
FIG. 13 is a sectional view of the socket component illustrated in FIG. 12, taken along line 13—13 of FIG. 12.
Figure 12:
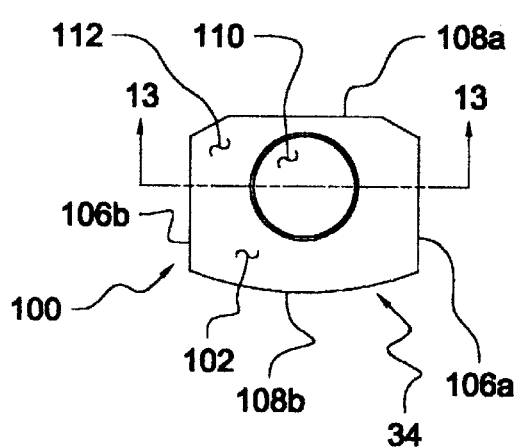
FIG. 12 is a bottom view of the socket component illustrated in FIG. 9.

The keel 120 extends from a location adjacent axially facing surface 108a toward axially facing surface 108b, preferably along a substantial portion of the support plate 100. As illustrated in FIG. 11, the keel 120 is preferably wedge-shaped, defining an outward taper as the keel 100 extends from a leading or insertion end 120a to trailing end 120b. Additionally, the insertion end 120a of keel 120 includes a beveled surface 122 to further aid in the implantation of the prosthetic joint 30. In another embodiment of the invention, the keel 120 may alternatively extend between the laterally facing surface 106a, 106b along a substantial portion of the support plate 100 to accommodate for insertion of the prosthetic joint 30 between adjacent vertebral bodies using a lateral approach. In a further embodiment of the invention, the keel 120 may be tapered along its height, either tapering inwardly from the bearing surface 104 to define a wedge shape or tapering outwardly from bearing surface 104 to define a dove-tail shape. In still another embodiment, the keel 120 may be configured as a winged keel, including a transverse portion extending across the main body portion of keel 120.

Keel 120 includes a pair of openings 126 extending therethrough to facilitate bone through-growth to enhance fixation to the adjacent vertebra. However, it should be understood that any number of openings 126 may be defined through the keel 120, including a single opening or three or more openings. It should also be understood that the openings 126 need not necessarily extend entirely through keel 120, but may alternatively extend partially therethrough. It should further be understood that the keel 120 need not necessarily define any openings 126 extending either partially or entirely therethrough. As discussed above, the surfaces of the articular component 34 that are in direct contact with vertebral bone are preferably coated with a bone-growth promoting substance, such as, for example, a hydroxyapatite coating. As also discussed above, the surfaces of the articular component 34 that are in direct contact with vertebral bone are preferably roughened prior to application of the bone-growth promoting substance.

Referring once again to FIG. 2, the projection or ball 60 of articular component 32 is at least partially disposed within the recess or socket 110 of articular component 34. The convex and concave articular surfaces of ball 60 and socket 110 abut one another in such a manner as to provide relative articulating motion between the articular components 32, 34. Specifically, the articular components 32, 34 are allowed to pivot and rotate relative to one another to maintain or restore motion substantially similar to the normal biomechanical motion provided by a natural intervertebral disc. The relative pivotal motion between the articular components 32, 34 is limited by the abutment of the conical surface 112 of component 34 against the planar surface 62 of component 32. During the articulating motion, the groove 70 formed along the ball 60 provides a passage for removing any matter, such as particulate debris, that may become lodged between the abutting articular surfaces of the components 32, 34. The groove 70 channels any such debris clear from the interfacing articular surfaces of the prosthetic joint 30 to prevent or at least reduce wear which otherwise might occur if foreign particles and/or built-up wear debris were to remain between the abutting portions of the articular surfaces.

Figure 15:
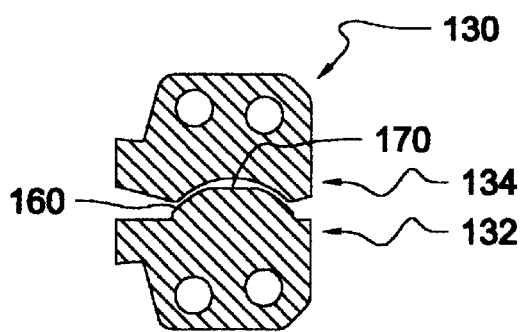
FIG. 15 is a sectional view of an intervertebral prosthetic joint according to another embodiment of the present invention.
Figure 16:
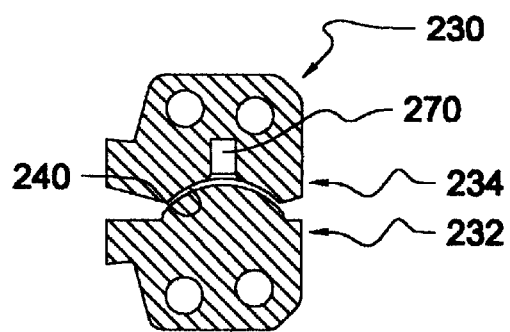
FIG. 16 is a sectional view of an intervertebral prosthetic joint according to a further embodiment of the present invention.

Referring to FIGS. 15 and 16, shown therein are intervertebral prosthetic joints according to other embodiments of the present invention. With regard to FIG. 15, shown therein is a prosthetic joint 130 including a first articular element 132 and a second articular element 134. Articular elements 132, 134 are similar to articular components 32, 34 in many respects except that the convex ball 160 of articular component 132 includes a flattened portion 170 extending along a portion of ball 160. The flattened portion 170 serves substantially the same purpose as the groove 70 extending along the ball 60; namely, to provide a means for removing any particulate debris that may become lodged between the abutting articular surfaces of components 132, 134. Although the flattened portion 170 is located at the approximate center of ball 160, it should be understood that the flattened portion 170 may be located anywhere along ball 160. It should also be understood that any number of flattened portions 170 may be formed along the ball 160, and that the ball 160 may include a combination of grooves 70 and flattened portions 170 to facilitate the removal of matter disposed between the abutting articular surfaces.

With regard to FIG. 16, shown therein is a prosthetic joint 230 including a first articular element 232 and a second articular element 234. Articular elements 232, 234 are similar to articular components 32, 34 in many respects except that the concave recess 240 of articular component 234 includes an opening 270 formed therein. The opening 270 serves substantially the same purpose as the groove 70 extending along the ball 60; namely, to provide a means for removing any particulate debris that may become lodged between the abutting articular surfaces of components 232, 234. Preferably, the opening 270 extends through the support plate 100 of the articular component 234 to channel any particulate debris that may become lodged between the abutting articular surfaces away from the ball-and-socket joint. The opening 270 may also extend through the keel 120 of the articular component 234. Although the opening 270 is illustrated as being located at the approximate center of the socket 240, it should be understood that the opening 270 may be located anywhere along socket 240 and at any orientation relative to socket 240. It should also be understood that any number of openings 270 may be formed along socket 240, and that the socket 240 may include a combination of grooves 70 and openings 270 to facilitate the removal of matter disposed between the abutting articular surfaces.

In further embodiments of the invention, either or both of the convex and concave articular surfaces of the components 32, 34 may define other types and configurations of surface depressions. For example, the surface depressions may be configured as multiple indentations or dimpling extending along one or both of the articular surfaces. In one specific embodiment, the convex articular surface may include multiple surface depressions such as may be found on the outer surface of a golf ball. However, it should be understood that many types and configurations of surface depressions may be used.

Referring to FIG. 17, shown therein is a lateral view of a portion of the spinal column, illustrating a pair of adjacent upper and lower vertebrae $V_U$, $V_L$ separated by a natural intervertebral disc D. As discussed above, in cases where the natural intervertebral disc D is diseased or degenerated, the natural disc D is typically removed via a discectomy or a similar surgical procedure, the details of which would be known to one of ordinary skill in the art.

As illustrated in FIGS. 18 and 19, removal of the diseased or degenerated disc D results in the formation of an intervertebral space S between the upper and lower vertebrae $V_U$, $V_L$. To accommodate insertion of the prosthetic joint 30 within the intervertebral space S, preparation of the upper and lower vertebrae $V_U$, $V_L$ is required to accept the prosthetic joint 30 therebetween. Specifically, elongate openings or slots 300 are formed along the vertebral endplates of the upper and lower vertebrae $V_U$, $V_L$ at a predetermined width w and to a predetermined depth d. In one embodiment of the invention, the elongate slots 300 are rectangular-shaped and extend from an anterior side 302 of the vertebrae $V_U$, $V_L$ toward a posterior side 304 of the vertebrae $V_U$, $V_L$. In a specific embodiment, the slots 300 are formed by chiseling or curetting. However, other methods of forming slots 300 are also contemplated as would occur to one of ordinary skill in the art, such as, for example, by drilling or reaming. In a preferred embodiment of the invention, the width w of the slots 300 is equal to or somewhat less than the corresponding width of the keels 80, 120 of articular components 32, 34. Additionally, the depth d of the slots 300 is preferably approximately equal to or slightly greater than the length of the keels 80, 120.

Figure 21:
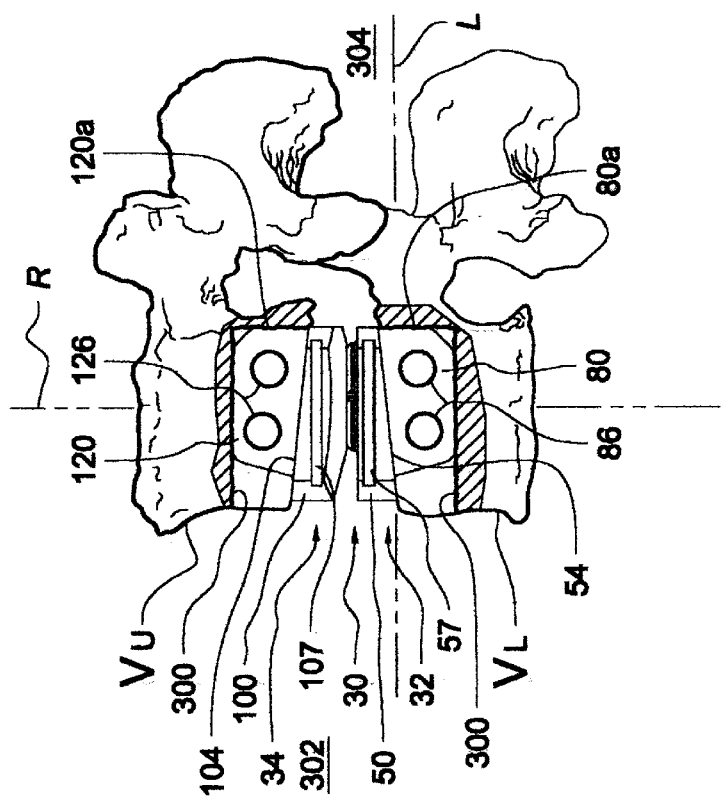
FIG. 21 is a partial sectional view of the portion of the spinal column shown in FIG. 18, illustrating implantation of the intervertebral prosthetic joint between the upper and lower vertebrae.
Figure 20:
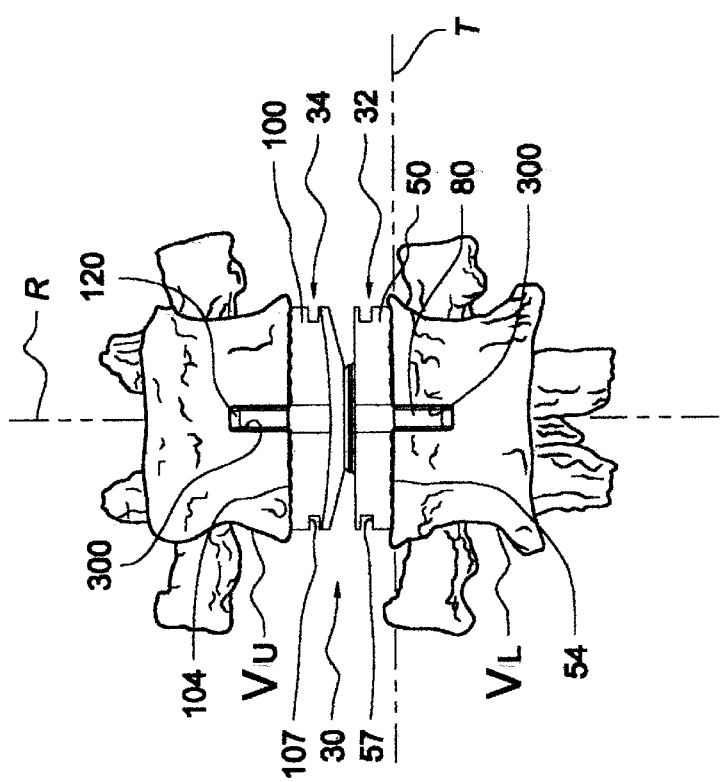
FIG. 20 is an anterior view of the portion of the spinal column shown in FIG. 18, illustrating implantation of the intervertebral prosthetic joint between the upper and lower vertebrae.

Referring to FIGS. 20 and 21, following preparation of the intervertebral space S, the articular components 32, 34 are inserted between the upper and lower vertebrae $V_U$, $V_L$. First, the articular components 32, 34 are placed in a predetermined relationship with respect to one another, preferably by an insertion instrument (not shown) or an equivalent tool that is adapted to engage the channels 57, 107 formed along a length of the support plates 50, 100. The insertion instrument (not shown) holds the articular components 32, 34 in a predetermined spatial relationship and at a predetermined orientation with respect to one another. The prosthetic joint 30 is inserted between the upper and lower vertebrae $V_U$, $V_L$ in a direction generally along the longitudinal axis L, with the keels 80, 120 of components 32, 34 being axially displaced along the slots 300. Notably, since the keels 80, 120 are axially displaced through the preformed slots 300, distraction of the upper and lower vertebrae $V_U$, $V_L$ to accommodate insertion of the prosthetic joint 30 is minimized, if not eliminated entirely.

As discussed above, the keels 80, 120 are tapered or wedge-shaped to facilitate insertion within the slots 300. The taper angle defined by each of the support plates 50, 100 also facilitates insertion of the prosthetic joint 30 within the intervertebral space S. Since the width w of the slots 300 is equal to or somewhat less than the corresponding width of the keels 80,120, the keels 80, 120 are effectively wedged within the slots 300. The depth d of the slots 300 formed in the upper and lower vertebrae $V_U$, $V_L$ correspondingly controls the positioning of the prosthetic joint 30 within the intervertebral space S. Specifically, proper positioning of the prosthetic joint 30 is accomplished when the insertion ends 80a, 120a of the keels 80, 120 bottom out against the end surfaces of slots 300. Controlling the insertion depth of the prosthetic joint 30 results in more precise positioning to avoid over-insertion or under-insertion of prosthetic joint 30. As discussed above, the angular positioning of the articular components 32, 34 relative to one another is dictated by the geometry of the upper and lower vertebrae $V_U$, $V_L$ and the particular location within the spinal column. As should be apparent, the distance between the support plates 50, 100 should be approximately equal to the height of the removed disc D, and the angular disposition of the support plates 50, 100 is dictated by the particular curvature or lordosis of the spinal column.

In the illustrated embodiment of the invention, the prosthetic joint 30 is implanted in the intervertebral space S via an anterior approach. However, it should be understood that the slots 300 may alternatively extend from the posterior side 304 of the vertebrae $V_U$, $V_L$ toward the anterior side 302 at a depth d, and the prosthetic joint 30 may alternatively be implanted in the intervertebral space S via a posterior approach. It should also understood that the slots 300 may alternatively extend from a first lateral side of the vertebrae $V_U$, $V_L$ toward the opposite lateral side of the vertebrae at a depth d, and the prosthetic joint 30 may alternatively be implanted in the intervertebral space S via a lateral approach.

Once the prosthetic joint 30 is inserted within the intervertebral space S, the articular components 32, 34 are initially secured to the upper and lower vertebrae $V_U$, $V_L$ via the disposition of the keels 80, 120 within the slots 300 formed in the vertebrae $V_U$, $V_L$ and by the compression forces exerted upon the bearing surfaces 54, 104 of the articular components 32, 34 by the adjacent vertebral endplates. The keels 80, 120 thus serve to resist migration or displacement of the prosthetic joint 30 relative to the adjacent vertebrae $V_U$, $V_L$. Subsequent to the implantation of prosthetic joint 30, the articular components 32, 34 are further secured to the upper and lower vertebrae $V_U$, $V_L$ via bone growth through the openings 86, 126 in keels 80, 120 and/or by bone on-growth onto the surfaces of the articular components 32, 34 that are in direct contact with vertebral bone. The bone through-growth and bone on-growth provide further resistance to the migration or displacement of the prosthetic joint 30 and prevent expulsion of the prosthetic joint 30 from the intervertebral space S. It should be understood that other means of engaging the prosthetic joint 30 to the upper and lower vertebrae $V_U$, $V_L$ are also contemplated, such as, for example, by bone screws, staples, an adhesive, or by other methods of engagement as would occur to one of ordinary skill in the art.

In use, the articular components 32, 34 cooperate with one another to provide a ball-and-socket type joint that permits relative pivotal and rotational movement therebetween, which correspondingly permits relative pivotal and rotational movement between the upper and lower vertebrae $V_U$, $V_L$. As a result, substantially normal biomechanical motion is restored to the portion of the spinal column being treated. Although the devices and methods of the present invention are particularly applicable to the lumbar region of the spine, it should nevertheless be understood that the present invention is also applicable to other portions of the spine, including the cervical or thoracic regions of the spine.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An intervertebral prosthetic joint, comprising:
    a first component adapted to engage a first vertebra and including a first articular surface; and
    a second component adapted to engage a second vertebra and including a second articular surface, said first and second articular surfaces cooperating to permit articulating motion between said first and second components; and
    wherein at least one of said first and second articular surfaces includes at least one surface depression configured to facilitate removal of matter disposed between abutting portions of said first and second articular surfaces.

2. The intervertebral prosthetic joint of claim 1, wherein said surface depression comprises a groove extendable beyond abutting portions of said first and second articular surfaces at some point during said articulating motion.

3. The intervertebral prosthetic joint of claim 1, wherein said surface depression comprises an opening in communication between said at least one of said first and second articular surfaces and a surface remote from abutting portions of said first and second articular surfaces.

4. The intervertebral prosthetic joint of claim 1, wherein one of said first and second articular surfaces comprises a convex surface, another of said first and second articular surfaces comprises a concave surface, at least a portion of said convex surface abutting at least a portion of said concave surface to permit said articulating motion.

5. The intervertebral prosthetic joint of claim 4, wherein said convex and concave surfaces are substantially spherical-shaped.

6. The intervertebral prosthetic joint of claim 5, wherein said surface depression comprises a groove extending inwardly from a circumference of at least one of said convex and concave surfaces.

7. The intervertebral prosthetic joint of claim 4, wherein said surface depression comprises a groove extending along at least a portion of said at least one of said convex and concave surfaces.

8. The intervertebral prosthetic joint of claim 7, wherein said groove extends inwardly from a periphery of said at least one of said convex and concave surfaces.

9. The intervertebral prosthetic joint of claim 7, wherein said groove is extendable beyond abutting portions of said convex and concave surfaces at some point during said articulating motion.

10. The intervertebral prosthetic joint of claim 7, wherein said groove extends across said at least one of said convex and concave surfaces to divide said at least one of said convex and concave surfaces into two distinct portions.

11. The intervertebral prosthetic joint of claim 10, wherein said distinct portions are substantially symmetrical.

12. The intervertebral prosthetic joint of claim 7, wherein said groove extends along said at least one of said convex and concave surfaces in a non-linear configuration.

13. The intervertebral prosthetic joint of claim 12, wherein said non-linear configuration is a curvilinear configuration.

14. The intervertebral prosthetic joint of claim 7, wherein a plurality of said grooves extends along said at least one of said convex and concave surfaces.

15. The intervertebral prosthetic joint of claim 7, wherein said groove extends along an outer contour of said at least one of said convex and concave surfaces.

16. The intervertebral prosthetic joint of claim 15, wherein said remote surface is a vertebral bearing surface configured to engage a corresponding one of the first and second vertebrae.

17. The intervertebral prosthetic joint of claim 7, wherein said groove has a length and a width, said length being greater than said width.

18. The intervertebral prosthetic joint of claim 4, wherein said surface depression comprises an opening in communication between said one of said convex and concave surfaces and a surface remote from said abutting portions of said first and second convex and concave surfaces.

19. The intervertebral prosthetic joint of claim 4, wherein a portion of said convex surface is flattened to form said surface depression.

20. The intervertebral prosthetic joint of claim 4, wherein at least one of said convex and concave surfaces is at least partially surrounded by a tapered surface to limit said articulating motion within a predetermined range of motion.

21. The intervertebral prosthetic joint of claim 20, wherein said tapered surface is a conical surface extending entirely about said at least one of said convex and concave surfaces.

22. The intervertebral prosthetic joint of claim 1, wherein each of said first and second components includes at least one channel configured to accept a corresponding portion of an insertion tool therein to maintain said first and second components at a predetermined position and at a predetermined orientation relative to one another during insertion of the prosthetic joint between the first and second vertebrae.

23. The intervertebral prosthetic joint of claim 1, wherein each of said first and second components includes a vertebral bearing surface and a flange extending from said vertebral bearing surface, said flange being adapted to penetrate a corresponding one of the first and second vertebrae, said flange defining at least one opening therethrough to permit bone growth through said flange.

24. The intervertebral prosthetic joint of claim 1, wherein the matter comprises particulate material.

25. An intervertebral prosthetic joint, comprising:
  a first articular component adapted to engage a first vertebra and including a projection; and
  a second articular component adapted to engage a second vertebra and including a recess, at least a portion of said projection being disposed within said recess to permit articulating motion between said first and second components; and
  wherein at least one of said projection and said recess defines at least one cavity configured to facilitate removal of matter disposed between said projection and said recess.

26. The intervertebral prosthetic joint of claim 25, wherein said projection includes a convex surface, and wherein said recess includes a concave surface, at least a portion of said convex surface abutting at least a portion of said concave recess to permit said articulating motion.

27. The intervertebral prosthetic joint of claim 26, wherein said cavity comprises a flattened portion extending along at least a portion of said generally convex surface.

28. The intervertebral prosthetic joint of claim 26, wherein said cavity comprises a groove extending along at least a portion of at least one of said convex and concave surfaces.

29. The intervertebral prosthetic joint of claim 26, wherein said cavity comprises an opening communicating between said one of said convex and concave surfaces and a surface remote from said at least one of said convex and concave surfaces.

30. An intervertebral prosthetic joint, comprising:
  a first articular component having a bearing surface adapted to engage a first vertebra; and
  a second articular component having a bearing surface adapted to engage a second vertebra; and
  wherein each of said first and second articular components includes a flange extending from said bearing surface and configured to penetrate a corresponding one of the first and second vertebrae, said flange defining at least one opening therethrough to permit bone growth through said flange.

31. The intervertebral prosthetic joint of claim 30, wherein said flange is positionable within a preformed opening in said corresponding one of the first and second vertebrae.

32. The intervertebral prosthetic joint of claim 31, wherein said flange has a length and is tapered along at least a portion of said length to facilitate insertion of said flange into said preformed opening.

33. The intervertebral prosthetic joint of claim 31, wherein said flange has a leading end, said leading end defining a beveled surface to facilitate insertion of said flange into said preformed opening.

34. The intervertebral prosthetic joint of claim 30, wherein each of said first and second articular components includes an articular surface disposed generally opposite said bearing surface, said articular surfaces cooperating to permit articulating motion between said first and second components.

35. The intervertebral prosthetic joint of claim 34, wherein at least one of said articular surfaces includes at least one surface depression to facilitate removal of matter disposed between said articular surfaces.

36. The intervertebral prosthetic joint of claim 35, wherein said surface depression is a groove extending along said at least one of said articular surfaces.

37. The intervertebral prosthetic joint of claim 36, wherein one of said first and second articular surfaces comprises a convex surface, another of said first and second articular surfaces comprises a concave surface, at least a portion of said convex surface abutting at least a portion of said concave surface to permit said articulating motion, said groove is extendable beyond said abutting portions of said convex and concave surfaces at some point during said articulating motion.

38. The intervertebral prosthetic joint of claim 30, wherein said flanges are coated with a bone-growth promoting substance to facilitate bone growth onto said flanges.

39. The intervertebral prosthetic joint of claim 30, wherein said flange defines a plurality of said openings therethrough.

40. An intervertebral prosthetic joint, comprising:

a first articular component including means for engaging a first vertebra; and a second articular component including means for engaging a second vertebra; and wherein said first and second articular components include surface means for permitting articulating motion therebetween, said surface means including means for removing matter disposed between abutting portions of said first and second articular components.

* * * * *

UNITED STATES PATENT AND TRADEMARK OFFICE
CERTIFICATE OF CORRECTION

PATENT NO. : 6,740,118 B2
DATED : May 25, 2004
INVENTOR(S) : Eisermann et al.

It is certified that error appears in the above-identified patent and that said Letters Patent is hereby corrected as shown below:

Column 13,
Line 5, replace "of'said" with -- of said --.

Signed and Sealed this

Twenty-eighth Day of September, 2004

JON W. DUDAS
*Director of the United States Patent and Trademark Office*

(12) EX PARTE REEXAMINATION CERTIFICATE (7677th)
United States Patent
Eisermann et al.

(10) Number: US 6,740,118 C1
(45) Certificate Issued: Aug. 10, 2010

(54) INTERVERTEBRAL PROSTHETIC JOINT

(75) Inventors: Lukas Eisermann, Memphis, TN (US); Eddie F. Ray, III, Collierville, TN (US)

(73) Assignee: Warsaw Orthopedic, Inc., Warsaw, IN (US)

Reexamination Request:
No. 90/010,579, Aug. 10, 2009

Reexamination Certificate for:
Patent No.: 6,740,118
Issued: May 25, 2004
Appl. No.: 10/042,589
Filed: Jan. 9, 2002

Certificate of Correction issued Sep. 28, 2004.

(51) Int. Cl.
*A61F 2/44* (2006.01)
*A61F 2/46* (2006.01)
*A61F 2/30* (2006.01)
*A61F 2/00* (2006.01)

(52) U.S. Cl. .................................................... 623/17.14
(58) Field of Classification Search .................... None
See application file for complete search history.

(56) References Cited

U.S. PATENT DOCUMENTS

| | | | |
|---|---|---|---|
| 1,641,059 A | 8/1927 | Tausch | |
| 3,320,951 A | 5/1967 | Wittebol | |
| 3,486,505 A | 12/1969 | Morrison | |
| 3,510,883 A | 5/1970 | Cathcart, III | |
| 3,740,769 A | 6/1973 | Haboush | |
| 3,903,549 A | 9/1975 | Deyerle | |
| 4,021,864 A | 5/1977 | Waugh | |
| 4,232,404 A | * 11/1980 | Samuelson et al. | 623/21.18 |
| 4,303,001 A | 12/1981 | Trungold | |
| 4,309,777 A | 1/1982 | Patil | |
| 4,318,627 A | 3/1982 | Morin | |
| 4,349,921 A | 9/1982 | Kuntz | |
| 4,470,158 A | 9/1984 | Pappas et al. | |
| 4,550,450 A | 11/1985 | Kinnett | |
| 4,622,959 A | 11/1986 | Marcus | |
| 4,624,674 A | * 11/1986 | Pappas et al. | 623/22.19 |
| 4,653,487 A | 3/1987 | Maale | |
| 4,681,589 A | 7/1987 | Tronzo | |
| 4,714,469 A | 12/1987 | Kenna | |
| 4,743,262 A | 5/1988 | Tronzo | |
| 4,759,766 A | 7/1988 | Buettner-Janz et al. | |
| 4,759,769 A | 7/1988 | Hedman et al. | |
| 4,770,661 A | 9/1988 | Oh | |
| 4,805,607 A | 2/1989 | Engelhardt et al. | |

(Continued)

FOREIGN PATENT DOCUMENTS

| | | |
|---|---|---|
| CH | 624573 | 8/1981 |
| DE | 2263842 | 7/1974 |
| DE | 2804936 | 8/1979 |

(Continued)

OTHER PUBLICATIONS

Pappas, Michael J. et al., Biomechanics and Design Rationale: The Buechel–Pappas Ankle Replacement System, Jan. 19, 2000.*

(Continued)

*Primary Examiner*—David O. Reip

(57) ABSTRACT

An intervertebral prosthetic joint including a first articular component adapted to engage a first vertebra and a second articular component adapted to engage a second vertebra. The articular components include abutting convex and concave articular surfaces that cooperate to permit articulating motion between the articular components. At least one of the convex and concave articular surfaces includes at least one surface depression that is configured to facilitate removal of matter disposed between abutting portions of the articular surfaces. In one embodiment of the prosthetic joint, each of the articular components has a vertebral bearing surface and a flange extending therefrom that is configured to penetrate a corresponding one of the first and second vertebrae, with the flange defining at least one opening extending therethrough to permit bone through-growth.

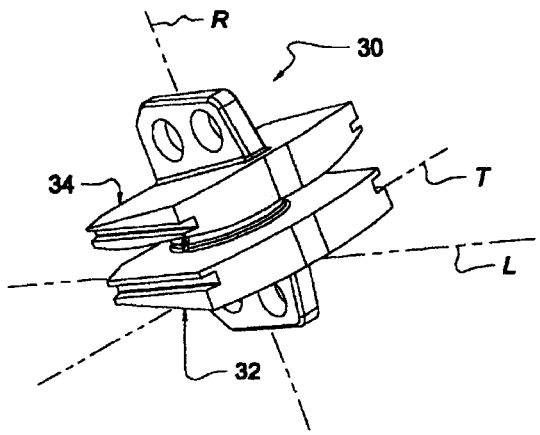

U.S. PATENT DOCUMENTS

| | | |
|---|---|---|
| 4,863,476 A | 9/1989 | Shepperd |
| 4,874,389 A | 10/1989 | Downey |
| 4,875,474 A | 10/1989 | Border |
| 4,892,545 A | 1/1990 | Day et al. |
| 4,932,969 A | 6/1990 | Frey et al. |
| 4,932,975 A | 6/1990 | Main et al. |
| 4,936,863 A | 6/1990 | Hofmann |
| 4,946,378 A | 8/1990 | Hirayama et al. |
| 4,958,970 A | 9/1990 | Rose et al. |
| 4,997,432 A | 3/1991 | Keller |
| 5,002,576 A | 3/1991 | Fuhrmann et al. |
| 5,004,476 A | 4/1991 | Cook |
| 5,034,254 A | 7/1991 | Cologna et al. |
| 5,035,716 A | 7/1991 | Downey |
| 5,037,438 A | 8/1991 | Davidson |
| 5,041,139 A * | 8/1991 | Brånemark ............... 623/21.18 |
| 5,047,055 A | 9/1991 | Bao et al. |
| 5,061,285 A | 10/1991 | Koch |
| 5,062,850 A | 11/1991 | MacMillan et al. |
| 5,071,437 A | 12/1991 | Steffee |
| 5,108,438 A | 4/1992 | Stone |
| 5,108,442 A | 4/1992 | Smith |
| 5,122,130 A | 6/1992 | Keller |
| 5,123,926 A | 6/1992 | Pisharodi |
| 5,147,404 A | 9/1992 | Downey |
| 5,171,278 A | 12/1992 | Pisharodi |
| 5,171,280 A | 12/1992 | Baumgartner |
| 5,171,281 A | 12/1992 | Parsons et al. |
| 5,192,326 A | 3/1993 | Bao et al. |
| 5,192,327 A | 3/1993 | Brantigan |
| 5,236,460 A | 8/1993 | Barber |
| 5,246,458 A | 9/1993 | Graham |
| 5,258,031 A | 11/1993 | Salib et al. |
| 5,271,737 A | 12/1993 | Baldwin et al. |
| 5,282,868 A | 2/1994 | Bahler |
| 5,290,312 A | 3/1994 | Kojimoto et al. |
| 5,306,308 A | 4/1994 | Gross et al. |
| 5,306,309 A | 4/1994 | Wagner et al. |
| 5,306,310 A | 4/1994 | Siebels |
| 5,314,477 A * | 5/1994 | Marnay ................... 623/17.15 |
| 5,320,644 A | 6/1994 | Baumgartner |
| 5,336,232 A | 8/1994 | Green et al. |
| 5,344,458 A | 9/1994 | Bonutti |
| 5,370,697 A | 12/1994 | Baumgartner |
| 5,375,823 A | 12/1994 | Navas |
| 5,390,683 A | 2/1995 | Pisharodi |
| 5,397,364 A | 3/1995 | Kozak et al. |
| 5,401,269 A | 3/1995 | Büttner-Janz et al. |
| 5,405,391 A | 4/1995 | Henderson et al. |
| 5,405,393 A | 4/1995 | Falkenstrom |
| 5,425,772 A | 6/1995 | Brantigan |
| 5,425,773 A | 6/1995 | Boyd et al. |
| 5,431,658 A | 7/1995 | Moskovich |
| 5,443,514 A | 8/1995 | Steffee |
| 5,443,515 A | 8/1995 | Cohen et al. |
| 5,458,638 A | 10/1995 | Kuslich et al. |
| 5,458,641 A | 10/1995 | Ramirez Jimenez |
| 5,458,642 A | 10/1995 | Beer et al. |
| 5,458,643 A | 10/1995 | Oka et al. |
| 5,480,442 A | 1/1996 | Bertagnoli |
| 5,484,437 A | 1/1996 | Michelson |
| 5,489,307 A | 2/1996 | Kuslich et al. |
| 5,489,308 A | 2/1996 | Kuslich et al. |
| 5,507,816 A | 4/1996 | Bullivant |
| 5,509,934 A | 4/1996 | Cohen |
| 5,522,899 A | 6/1996 | Michelson |
| 5,534,028 A | 7/1996 | Bao et al. |
| 5,534,029 A | 7/1996 | Shima |
| 5,534,030 A | 7/1996 | Navarro et al. |
| 5,534,031 A | 7/1996 | Matsuzaki et al. |
| 5,535,861 A | 7/1996 | Young |
| 5,545,229 A | 8/1996 | Parsons et al. |
| 5,549,679 A | 8/1996 | Kuslich |
| 5,549,680 A | 8/1996 | Gordon |
| 5,554,191 A | 9/1996 | Lahille et al. |
| 5,556,431 A | 9/1996 | Büttner-Janz |
| 5,562,736 A | 10/1996 | Ray et al. |
| 5,562,737 A | 10/1996 | Graf |
| 5,562,738 A | 10/1996 | Boyd et al. |
| 5,571,109 A | 11/1996 | Bertagnoli |
| 5,571,190 A | 11/1996 | Ulrich et al. |
| 5,571,192 A | 11/1996 | Schonhoffer |
| 5,591,235 A | 1/1997 | Kuslich |
| 5,593,444 A | 1/1997 | Svensson et al. |
| 5,609,635 A * | 3/1997 | Michelson ................ 623/17.16 |
| 5,609,636 A | 3/1997 | Kohrs et al. |
| 5,609,637 A | 3/1997 | Biedermann et al. |
| 5,609,638 A | 3/1997 | Price et al. |
| 5,645,596 A | 7/1997 | Kim et al. |
| 5,653,763 A | 8/1997 | Errico et al. |
| 5,658,335 A | 8/1997 | Allen |
| 5,658,336 A | 8/1997 | Pisharodi |
| 5,658,337 A | 8/1997 | Kohrs et al. |
| 5,658,347 A | 8/1997 | Sarkisian et al. |
| 5,665,122 A | 9/1997 | Kambin |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |
| 5,676,702 A | 10/1997 | Ratron |
| 5,683,463 A | 11/1997 | Godefroy et al. |
| 5,683,464 A | 11/1997 | Wagner et al. |
| 5,683,465 A | 11/1997 | Shinn et al. |
| 5,693,100 A | 12/1997 | Pisharodi |
| 5,702,449 A | 12/1997 | McKay |
| 5,702,450 A | 12/1997 | Bisserie |
| 5,702,451 A | 12/1997 | Biedermann et al. |
| 5,702,453 A | 12/1997 | Rabbe et al. |
| 5,702,455 A | 12/1997 | Saggar |
| 5,702,469 A | 12/1997 | Whipple et al. |
| 5,702,486 A | 12/1997 | Craig et al. |
| 5,716,415 A | 2/1998 | Steffee |
| 5,716,416 A | 2/1998 | Lin |
| 5,720,751 A | 2/1998 | Jackson |
| 5,722,977 A | 3/1998 | Wilhelmy |
| 5,723,013 A | 3/1998 | Jeanson et al. |
| 5,728,157 A | 3/1998 | Prescott |
| 5,749,916 A | 5/1998 | Richelsoph |
| 5,755,796 A | 5/1998 | Ibo et al. |
| 5,755,797 A | 5/1998 | Baumgartner |
| 5,755,798 A | 5/1998 | Papavero et al. |
| 5,755,811 A | 5/1998 | Tanamal et al. |
| 5,766,252 A | 6/1998 | Henry et al. |
| 5,766,253 A | 6/1998 | Brosnahan, III |
| 5,776,199 A | 7/1998 | Michelson |
| 5,782,830 A | 7/1998 | Farris |
| 5,782,832 A | 7/1998 | Larsen et al. |
| 5,797,909 A | 8/1998 | Michelson |
| 5,800,547 A | 9/1998 | Schafer et al. |
| 5,800,550 A | 9/1998 | Sertich |
| 5,824,094 A | 10/1998 | Serhan et al. |
| 5,827,328 A | 10/1998 | Buttermann |
| 5,861,041 A | 1/1999 | Tienboon |
| 5,865,845 A | 2/1999 | Thalgott |
| 5,865,846 A | 2/1999 | Bryan et al. |
| 5,865,847 A | 2/1999 | Kohrs et al. |
| 5,865,848 A | 2/1999 | Baker |
| 5,876,447 A | 3/1999 | Arnett |
| 5,876,457 A | 3/1999 | Picha et al. |
| 5,888,222 A | 3/1999 | Coates et al. |
| 5,888,224 A | 3/1999 | Beckers et al. |

| Patent | Date | Name |
|---|---|---|
| 5,888,226 A | 3/1999 | Rogozinski |
| 5,888,227 A | 3/1999 | Cottle |
| 5,888,228 A | 3/1999 | Knothe et al. |
| 5,893,889 A | 4/1999 | Harrington |
| 5,893,890 A | 4/1999 | Pisharodi |
| 5,895,426 A | 4/1999 | Scarborough et al. |
| 5,895,428 A | 4/1999 | Berry |
| 5,897,593 A | 4/1999 | Kohrs et al. |
| 5,899,941 A | 5/1999 | Nishijima et al. |
| 5,904,719 A | 5/1999 | Errico et al. |
| 5,916,267 A | 6/1999 | Tienboon |
| 5,916,269 A * | 6/1999 | Serbousek et al. ....... 623/22.24 |
| 5,919,235 A | 7/1999 | Husson et al. |
| 5,928,284 A | 7/1999 | Mehdizadeh |
| 5,961,554 A | 10/1999 | Janson et al. |
| 5,964,807 A | 10/1999 | Gan et al. |
| 5,972,031 A | 10/1999 | Biedermann et al. |
| 5,976,186 A | 11/1999 | Bao et al. |
| 5,980,522 A | 11/1999 | Koros et al. |
| 5,980,572 A | 11/1999 | Kim et al. |
| 5,984,967 A | 11/1999 | Zdeblick et al. |
| 5,989,289 A | 11/1999 | Coates et al. |
| 5,989,290 A | 11/1999 | Biedermann et al. |
| 5,989,291 A | 11/1999 | Ralph et al. |
| 5,989,292 A | 11/1999 | Van Loon |
| 6,001,130 A | 12/1999 | Bryan et al. |
| 6,010,502 A | 1/2000 | Bagby |
| 6,015,436 A | 1/2000 | Schonhoffer |
| 6,019,792 A | 2/2000 | Cauthen |
| 6,019,793 A | 2/2000 | Perren et al. |
| 6,022,376 A | 2/2000 | Assell et al. |
| 6,033,438 A | 3/2000 | Bianchi et al. |
| 6,039,761 A | 3/2000 | Li et al. |
| 6,039,763 A | 3/2000 | Shelokov |
| 6,045,579 A | 4/2000 | Hochshuler et al. |
| 6,045,580 A | 4/2000 | Scarborough et al. |
| 6,045,581 A * | 4/2000 | Burkinshaw ............ 623/18.11 |
| 6,059,790 A | 5/2000 | Sand et al. |
| 6,059,829 A | 5/2000 | Schlapfer et al. |
| 6,063,121 A | 5/2000 | Xavier et al. |
| 6,066,175 A | 5/2000 | Henderson et al. |
| 6,068,630 A | 5/2000 | Zucherman et al. |
| RE36,758 E | 6/2000 | Fitz |
| 6,074,390 A | 6/2000 | Zucherman et al. |
| 6,074,423 A | 6/2000 | Lawson |
| 6,080,155 A | 6/2000 | Michelson |
| 6,080,193 A | 6/2000 | Hochshuler et al. |
| 6,083,225 A | 7/2000 | Winslow et al. |
| 6,086,595 A | 7/2000 | Yonemura et al. |
| 6,086,613 A | 7/2000 | Camino et al. |
| 6,090,112 A | 7/2000 | Zucherman et al. |
| 6,090,143 A | 7/2000 | Meriwether et al. |
| 6,093,205 A | 7/2000 | McLeod et al. |
| 6,093,207 A | 7/2000 | Pisharodi |
| 6,096,080 A | 8/2000 | Nicholson et al. |
| 6,099,531 A | 8/2000 | Bonutti |
| 6,102,949 A | 8/2000 | Biedermann et al. |
| 6,102,950 A | 8/2000 | Vaccaro |
| 6,102,954 A | 8/2000 | Albrektsson et al. |
| 6,110,210 A | 8/2000 | Norton et al. |
| 6,111,164 A | 8/2000 | Rainey et al. |
| 6,113,637 A | 9/2000 | Gill et al. |
| 6,113,638 A | 9/2000 | Williams et al. |
| 6,113,639 A | 9/2000 | Ray et al. |
| 6,117,174 A | 9/2000 | Nolan |
| 6,120,506 A | 9/2000 | Kohrs et al. |
| 6,123,705 A | 9/2000 | Michelson |
| 6,126,688 A | 10/2000 | McDonnell |
| 6,129,763 A | 10/2000 | Chauvin et al. |
| 6,132,465 A | 10/2000 | Ray et al. |
| 6,132,466 A | 10/2000 | Hoffman et al. |
| 6,136,031 A | 10/2000 | Middleton |
| 6,139,579 A | 10/2000 | Steffee et al. |
| 6,143,031 A | 11/2000 | Knothe et al. |
| 6,143,032 A | 11/2000 | Schafer et al. |
| 6,143,033 A | 11/2000 | Paul et al. |
| 6,146,420 A | 11/2000 | McKay |
| 6,146,421 A | 11/2000 | Gordon et al. |
| 6,146,422 A | 11/2000 | Lawson |
| 6,149,651 A | 11/2000 | Drewry et al. |
| 6,149,686 A | 11/2000 | Kuslich et al. |
| 6,156,038 A | 12/2000 | Zucherman et al. |
| 6,156,067 A | 12/2000 | Bryan et al. |
| 6,159,211 A | 12/2000 | Boriani et al. |
| 6,159,215 A | 12/2000 | Urbahns et al. |
| 6,162,252 A | 12/2000 | Kuras et al. |
| 6,165,219 A | 12/2000 | Kohrs et al. |
| 6,168,631 B1 | 1/2001 | Maxwell et al. |
| 6,174,311 B1 | 1/2001 | Branch et al. |
| 6,174,334 B1 | 1/2001 | Suddaby |
| 6,179,873 B1 | 1/2001 | Zientek |
| 6,179,874 B1 | 1/2001 | Cauthen |
| 6,179,875 B1 | 1/2001 | Von Strempel |
| 6,183,517 B1 | 2/2001 | Suddaby |
| 6,187,048 B1 | 2/2001 | Milner et al. |
| 6,190,413 B1 | 2/2001 | Sutcliffe |
| 6,190,414 B1 | 2/2001 | Young et al. |
| 6,193,755 B1 | 2/2001 | Metz-Stavenhagen et al. |
| 6,193,756 B1 | 2/2001 | Studer et al. |
| 6,193,757 B1 | 2/2001 | Foley et al. |
| 6,206,922 B1 | 3/2001 | Zdeblick et al. |
| 6,210,442 B1 | 4/2001 | Wing et al. |
| 6,214,005 B1 | 4/2001 | Benzel et al. |
| 6,214,050 B1 | 4/2001 | Huene |
| 6,224,599 B1 | 5/2001 | Baynham et al. |
| 6,224,631 B1 | 5/2001 | Kohrs |
| 6,228,118 B1 | 5/2001 | Gordon |
| 6,231,609 B1 | 5/2001 | Mehdizadeh |
| 6,235,059 B1 | 5/2001 | Benezech et al. |
| 6,238,414 B1 | 5/2001 | Griffiths |
| 6,241,769 B1 | 6/2001 | Nicholson et al. |
| 6,241,770 B1 | 6/2001 | Michelson |
| 6,241,771 B1 | 6/2001 | Gresser et al. |
| 6,248,131 B1 | 6/2001 | Felt et al. |
| 6,251,140 B1 | 6/2001 | Marino et al. |
| 6,264,655 B1 | 7/2001 | Pisharodi |
| 6,277,149 B1 | 8/2001 | Boyle et al. |
| 6,277,150 B1 | 8/2001 | Crawley et al. |
| 6,283,998 B1 | 9/2001 | Eaton |
| 6,290,724 B1 | 9/2001 | Marino |
| 6,302,914 B1 | 10/2001 | Michelson |
| 6,309,421 B1 | 10/2001 | Pisharodi |
| RE37,479 E | 12/2001 | Kuslich |
| 6,325,827 B1 | 12/2001 | Lin |
| 6,344,057 B1 | 2/2002 | Rabbe et al. |
| 6,368,325 B1 | 4/2002 | McKinley et al. |
| 6,368,350 B1 | 4/2002 | Erickson et al. |
| 6,368,351 B1 | 4/2002 | Glenn et al. |
| 6,368,353 B1 | 4/2002 | Arcand |
| 6,371,987 B1 | 4/2002 | Weiland et al. |
| 6,375,681 B1 | 4/2002 | Truscott |
| 6,402,785 B1 | 6/2002 | Zdeblick et al. |
| 6,413,278 B1 | 7/2002 | Marchosky |
| 6,419,705 B1 | 7/2002 | Erickson |
| 6,423,095 B1 | 7/2002 | Van Hoeck et al. |
| 6,440,142 B1 | 8/2002 | Ralph et al. |
| 6,440,168 B1 | 8/2002 | Cauthen |
| 6,447,547 B1 | 9/2002 | Michelson |
| 6,468,310 B1 | 10/2002 | Ralph et al. |
| 6,478,800 B1 | 11/2002 | Fraser et al. |
| 6,478,801 B1 | 11/2002 | Ralph et al. |
| 6,482,233 B1 | 11/2002 | Aebi et al. |

| | | | |
|---|---|---|---|
| 6,485,491 | B1 | 11/2002 | Farris et al. |
| 6,488,710 | B2 | 12/2002 | Besselink |
| 6,503,279 | B1 | 1/2003 | Webb et al. |
| 6,517,580 | B1 | 2/2003 | Ramadan et al. |
| 6,520,990 | B1 | 2/2003 | Ray |
| 6,547,823 | B2 | 4/2003 | Scarborough et al. |
| 6,572,653 | B1 | 6/2003 | Simonson |
| 6,582,715 | B1 | 6/2003 | Barry et al. |
| 6,592,624 | B1 | 7/2003 | Fraser et al. |
| 6,595,995 | B2 | 7/2003 | Zdeblick et al. |
| 6,602,291 | B1 | 8/2003 | Ray et al. |
| 6,610,065 | B1 | 8/2003 | Branch et al. |
| 6,638,310 | B2 | 10/2003 | Lin et al. |
| 6,641,614 | B1 | 11/2003 | Wagner et al. |
| 6,706,070 | B1 | 3/2004 | Wagner et al. |
| 6,719,794 | B2 | 4/2004 | Gerber et al. |
| 6,733,505 | B2 | 5/2004 | Li |
| 6,743,256 | B2 | 6/2004 | Mason |
| 6,755,841 | B2 | 6/2004 | Fraser et al. |
| 6,770,074 | B2 | 8/2004 | Michelson |
| 6,824,565 | B2 | 11/2004 | Muhanna et al. |
| 6,863,689 | B2 | 3/2005 | Ralph et al. |
| 6,875,213 | B2 | 4/2005 | Michelson |
| 6,923,810 | B1 | 8/2005 | Michelson |
| 6,936,071 | B1 | 8/2005 | Marnay et al. |
| 6,963,071 | B2 | 11/2005 | Bristol |
| 6,964,687 | B1 | 11/2005 | Bernard et al. |
| 6,966,912 | B2 | 11/2005 | Michelson |
| 7,081,120 | B2 | 7/2006 | Li et al. |
| 7,118,580 | B1 | 10/2006 | Beyersdorff et al. |
| 7,169,182 | B2 | 1/2007 | Errico et al. |
| 7,238,203 | B2 | 7/2007 | Bagga et al. |
| 7,575,576 | B2 | 8/2009 | Zubok et al. |
| 2002/0035400 | A1 | 3/2002 | Bryan et al. |
| 2002/0120273 | A1 | 8/2002 | Needham et al. |
| 2003/0083747 | A1 | 5/2003 | Winterbottom et al. |
| 2003/0135275 | A1 | 7/2003 | Garcia et al. |
| 2005/0021042 | A1 | 1/2005 | Mamay et al. |
| 2005/0143747 | A1 | 6/2005 | Zubok et al. |

FOREIGN PATENT DOCUMENTS

| | | | |
|---|---|---|---|
| DE | 3023353 | | 4/1981 |
| DE | 3526742 | | 1/1987 |
| DE | 32 28 690 | | 2/1995 |
| DE | 29911422 | | 9/1999 |
| EP | 0333990 | | 9/1989 |
| EP | 0 471 821 | | 2/1992 |
| EP | 0599419 | | 1/1994 |
| FR | 2718635 | | 10/1995 |
| FR | 2724108 | | 3/1996 |
| FR | 2737656 | | 2/1997 |
| FR | 2742653 | | 6/1997 |
| FR | 2795945 | | 1/2001 |
| JP | 2261446 | | 10/1990 |
| WO | 9723175 | | 7/1977 |
| WO | WO 91/07931 | * | 9/1991 |
| WO | 91/13598 | | 9/1991 |
| WO | 9310725 | | 6/1993 |
| WO | 98/34552 | | 8/1998 |
| WO | 0101893 | | 1/2001 |
| WO | 01/19295 | | 3/2001 |
| WO | 0164142 | | 9/2001 |
| WO | 03059212 | | 7/2002 |
| WO | 02/071986 | | 9/2002 |
| WO | 03/053290 | | 7/2003 |

OTHER PUBLICATIONS

Hallab, Nadim et al., Biomaterial Optimization in Total Disc Arthroplasty, SPINE, vol. 28, No. 205, pp. S139–S152, 2003.*

Tooms, Robert E., "Arthroplasty of Ankle and Knee," Campbell's Operative Orthopaedics, Seventh Edition, vol. Two, Chapter 40, pp. 1145–1152 (1987).

R.S. Laskin, Tricon–M Uncemented Total Knee Arthroplasty, A Review of 96 Knees Followed for Longer Than 2 Years, Journal of Arthroplasty, vol. 3, No. 1, Mar. 1988, pp. 27–38.

R.G. Volz, et al., The Mechanical Stability of Various Noncemented Tibial Components, Clinical Orthopaedics and Related Research, No. 226, Jan. 1988.

J.T. Møller, et al., Total Condylar Prosthesis Placement in Knee Arthroplasty, Acta orthop. scand. 54, 708–713, 1983.

D.C. McKeever, The Classic Tibial Plateau Prosthesis, Clinical Orthopaedics and Related Research, No. 192, Jan.–Feb. 1985, pp. 3–12.

E.G. Little, et al., An experimental technique for the investigation of three–dimensional stress in bone cement underlying a tibial plateau, Proc Instn Mech Engrs, vol. 203, pp. 35–41.

R.V. Kenna, et al., Design Rational for the Porous Coated Anatomic Total Knee System, pp. 71–88.

Zimmer Advertisement, The Journal of Bone and Joint Surgery, vol. 52–A, No. 5 (Jul. 1970).

Zimmer Advertisement, The Journal of Bone and Joint Surgery, vol. 53–A, No. 6 (Sep. 1971).

Mamay, L'Arthroplastie Intervertebrale Lombaire, La Revue De Medecine Orthopedique, No. 25, Jun.–Sep. 1991.

J.L. Sbarbaro Jr. Hemi–tibial Plateau Prosthesis Ten Years Experience in 500 Knee Arthroplastics, Acta Orthopedica Belgica, Tume 39 Fasc. 1, pp. 91–101 (1973).

A.B. Swanson et al., Unicompartmental and Biocompartmental Arthroplasty of the Knee with a Finned Metal Tibial–Plateau Implant, The Journal of Bone & Joint Surgery, vol. 67–A, No. 8, Oct. 1985.

Intermedics Orthopedics Advertisement, The Journal of Bone and Joint Surgery, vol. 68A, No. 1 (Jan. 1986).

Dow Corning Wright Advertisement, The Journal of Bone and Joint Surgery, American vol. 68A, No. 1 (Jan. 1986).

Neer II Advertisement, The Journal of Bone and Joint Surgery, American vol. 68A, No. 1 (Jan. 1986).

Seipi Advertisement, The Journal of Bone and Joint Surgery, British vol. 72–B, No. One (Jan. 1990).

Biomet Advertisement, The Journal of Bone and Joint Surgery, American vol. 72–A, No. 1 (Jan. 1990).

Accord Advertisement, The Journal of Bone and Joint Surgery, British vol. 72–B, No. Two (Mar. 1990).

P.F.C. Advertisement, The Journal of Bone and Joint Surgery, British vol. 72–B, No. Two (Mar. 1990).

Osteonics Advertisement, The Journal of Bone and Joint Surgery, American vol. 74–A, No. 1 (Jan. 1992).

Sutter Advertisement, The Journal of Books and Joint Surgery, American vol. 74–A, No. 1 (Jan. 1992).

Smith & Newphew Advertisement, The Journal of Bone and Joint Surgery, American vol. 74–A, No. 1 (Jan. 1992).

DePuy Advertisements, The Journal of Bone and Joint Surgery, American vol. 74–A, No. 1 (Jan. 1992).

DePuy Advertisements, The Journal of Bone and Joint Surgery, American vol. 70–A, No. 1 (Jan. 1988).

Johnson & Johnson Advertisement, The Journal of Bone and Joint Surgery, American vol. 70–A, No. 2 (Feb. 1988).

Johnson & Johnson Advertisement, The Journal of Bone and Joint Surgery, American vol. 68–A, No. 2 (Feb. 1986).

Homedica Advertisement, Johnson & Johnson Advertisement, The Journal of Bone and Joint Surgery, American vol. 68–A, No. 2 (Feb. 1986).

J.L. Sbarbaro, Jr., Press Fit Implant Arthroplasty of the Hip and Knee, J. Biomedi Mater. Res. Symposium, No. 5 (Part 2) pp. 285–288 (1974).

T. Hoogland, et al., Total Lumbar Intervertebral Disc Replacement: Testing of a New Articulating Spacer in Human Cadaver Spine, 24th Annual ORS, Dallas, Texas, Feb. 21–23, 102 (1978).

Mark Szpalski, et al., Spine Arthroplasty: a historical review, Eur Spine J (2002).

Anthony G. Viscogliosi, et al., Spine Arthroplasty: Spine Industry Analysis Series, Viscogliosi Bros., LLC, (Nov. 2001).

Jeanette E. Ahren, Ph.D., et al., Normal Joint Mobility is Maintained with an Artificial Disc Prothesis, Link (1999).

Backup: Spinal Arthroplasty, Springer (Jan. 2001).

David S. Hungerford, M.D., et al., Preliminary Experience with a Total Knee Prosthesis with Porous Coating Used without Cement, Clinical Orthopedics and Related Research, No. 176, Jun. 1983, pp. 95–107.

* cited by examiner

US 6,740,118 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 4, 6, 7, 9-16, 18, 19, 25-29 and 40 are cancelled.

Claims 1, 5, 8, 17, 20 and 30 are determined to be patentable as amended.

Claims 3, 21-24 and 31-39, dependent on an amended claim, are determined to be patentable.

New claims 41-77 are added and determined to be patentable.

1. An intervertebral prosthetic joint, comprising:
   a first component adapted to engage a first vertebra and including a [first] *convex* articular surface; and
   a second component adapted to engage a second vertebra and including a [second] *concave* articular surface, said [first] *convex* and [second] *concave* articular surfaces cooperating to permit articulating motion between said first and second components; and
   wherein [at least one of] said [first and second] *convex* articular [surfaces] *surface* includes [at least one] *a* surface depression *in the form of a single curvilinear groove having a first end which extends beyond abutting portions of said convex and concave articular surfaces at some point during articulating motion of said prosthetic joint and a second end, said single curvilinear groove not extending across the entire convex articular surface, and said single curvilinear groove being* configured to facilitate removal of matter disposed between abutting portions of said [first] *convex* and [second] *concave* articular surfaces.

5. The intervertebral prosthetic joint of claim [4] *1*, wherein said convex and concave surfaces are substantially spherical-shaped.

8. The intervertebral prosthetic joint of claim [7] *1*, wherein said groove extends inwardly from a periphery of [said at least one of] said convex [and concave surfaces] *surface*.

17. The intervertebral prosthetic joint of claim [7] *1*, wherein said groove has a length and a width, said length being greater than said width.

20. The intervertebral prosthetic joint of claim [4] *1*, wherein at least one of said convex and concave surfaces is at least partially surrounded by a tapered surface to limit said articulating motion within a predetermined range of motion.

30. An intervertebral prosthetic joint, comprising:
   a first articular component having (i) a bearing *side comprising a bearing* surface adapted to engage a first vertebra *and (ii) a joint side comprising an articular surface and a surrounding surface surrounding said articular surface*; and
   a second articular component having (i) a bearing *side comprising a bearing* surface adapted to engage a second vertebra *and (ii) a joint side comprising an articular surface and a surrounding surface surrounding said articular surface*; and
   wherein each of said first and second articular components includes a flange extending from said bearing surface and configured to penetrate a corresponding one of the first and second vertebrae, said flange defining at least one opening therethrough to permit bone growth through said flange,
   *wherein, with respect to said first articular component, said bearing surface and said surrounding surface are angled to define a continuous taper such that, when implanted, a narrow end of said taper is positioned at a posterior position relative to the first vertebra and a wide end of said taper is positioned at an anterior position relative to the first vertebra, and*
   *wherein, with respect to said second articular component, said bearing surface and said surrounding surface are parallel.*

41. *The intervertebral prosthetic joint of claim 1, wherein said curvilinear groove curves in only one direction along its length.*

42. *The intervertebral prosthetic joint of claim 41, wherein said curvilinear groove has a radiused bottom surface.*

43. *The intervertebral prosthetic joint of claim 41, wherein said curvilinear groove extends from an edge of said convex articular surface.*

44. *The intervertebral prosthetic joint of claim 41, wherein said curvilinear groove is approximately 0.75 mm deep.*

45. *The intervertebral prosthetic joint of claim 44, wherein said curvilinear groove is approximately 0.4 mm wide.*

46. *The intervertebral prosthetic joint of claim 41, wherein said first component has (i) a bearing side comprising a bearing surface adapted to engage the first vertebra and (ii) a joint side comprising said convex articular surface and a separate surface positioned around said convex articular surface,*
   *wherein said bearing surface and said separate surface are angled to define a taper such that, when implanted, a narrow end of said taper is positioned at a posterior position of the first vertebra and a wide end of said taper is positioned at an anterior position of the first vertebra.*

47. *The intervertebral prosthetic joint of claim 41, wherein each of said first and second components includes a flange extending from a bearing surface and configured to penetrate a corresponding one of the first and second vertebrae, said flange defining at least one opening therethrough to permit bone growth through said flange,*
   *wherein each of said flanges comprises (i) a leading end, extending up from said bearing surface, (ii) a trailing end, extending up from said bearing surface, and (iii) a top edge, extending between said leading and trailing ends,*
   *wherein said top edge defines a continuous linear edge between said leading and trailing ends, and*
   *wherein said leading end comprises an edge angled away from a normal of said bearing surface toward said trailing end.*

48. *The intervertebral prosthetic joint of claim 47, wherein a transition between said angled edge and said top* edge is rounded, and a transition between said trailing end and said top edge is rounded.

49. The intervertebral prosthetic joint of claim 48, wherein each of said bearing surfaces comprises a roughened surface.

50. The intervertebral prosthetic joint of claim 49, wherein said first articular component is a unitary body.

51. The intervertebral prosthetic joint of claim 30, wherein a taper angle of said taper is about 3°.

52. The intervertebral prosthetic joint of claim 30, wherein a taper angle of said taper is about 6°.

53. The intervertebral prosthetic joint of claim 30, wherein said taper corresponds to a lordotic angle of a portion of the spinal column in which said prosthetic joint is used.

54. The intervertebral prosthetic joint of claim 30, wherein each of said flanges comprises (i) a leading end, extending up from said bearing surface, (ii) a trailing end, extending up from said bearing surface, and (iii) a top edge, extending between said leading and trailing ends,
wherein said top edge defines a continuous linear edge between said leading and trailing ends, and
wherein said leading end comprises an edge angled away from a normal of said bearing surface toward said trailing end.

55. The intervertebral prosthetic joint of claim 54, wherein a transition between said angled edge and said top edge is rounded, and a transition between said trailing end and said top edge is rounded.

56. The intervertebral prosthetic joint of claim 30, wherein each of said bearing surfaces comprises a roughened surface.

57. The intervertebral prosthetic joint of claim 30, wherein said articular and surrounding surfaces of said first articular component are contiguous and said first articular component is a unitary body.

58. An intervertebral prosthetic joint, comprising:
a first articular component having (i) a bearing side comprising a bearing surface adapted to engage a first vertebra and (ii) a joint side comprising an articular surface and a surrounding surface surrounding said articular surface; and
a second articular component having (i) a bearing side comprising a bearing surface adapted to engage a second vertebra and (ii) a joint side comprising an articular surface and a surrounding surface surrounding said articular surface; and
wherein each of said first and second articular components includes a flange extending from said bearing surface and configured to penetrate a corresponding one of the first and second vertebrae, said flange defining at least one opening therethrough to permit bone growth through said flange,
wherein, with respect to said first articular component, said bearing surface and said surrounding surface are angled to define a taper between an anterior end and a posterior end of said first articular component, when implanted, such that a distance between said bearing surface and said surrounding surface at a first cross-section at a posterior side of said first articular component is less than at a second cross-section at a middle position, and a distance between said bearing surface and said surrounding surface is less at said second cross-section than at a third cross-section at an anterior side of said first articular component,
wherein said first, second and third cross-sections are parallel with each other and perpendicular to a direction of the taper, and wherein, with respect to said second articular component, said bearing surface and said surrounding surface are parallel.

59. The intervertebral prosthetic joint of claim 58, wherein each of said flanges comprises (i) a leading end, extending up from said bearing surface, (ii) a trailing end, extending up from said bearing surface, and (iii) a top edge, extending between said leading and trailing ends,
wherein said top edge defines a continuous linear edge between said leading and trailing ends, and
wherein said leading end comprises an edge angled away from a normal of said bearing surface toward said trailing end.

60. The intervertebral prosthetic joint of claim 59, wherein a transition between said angled edge and said top edge is rounded, and a transition between said trailing end and said top edge is rounded.

61. The intervertebral prosthetic joint of claim 60, wherein each of said bearing surfaces comprises a roughened surface.

62. The intervertebral prosthetic joint of claim 61, wherein said articular surface of said first articular component has a single curvilinear groove, said groove having a first end which extends beyond abutting portions of said articular surfaces at some point during articulating motion of said prosthetic joint and a second end which does not extend across the entire articular surface of said first articular component.

63. The intervertebral prosthetic joint of claim 61, wherein said taper corresponds to a lordotic angle of a portion of the spinal column in which said prosthetic joint is used.

64. The intervertebral prosthetic joint of claim 63, wherein a taper angle of said taper is about 3°.

65. The intervertebral prosthetic joint of claim 63, wherein a taper angle of said taper is about 6°.

66. The intervertebral prosthetic joint of claim 62, wherein said bearing surfaces are substantially planar.

67. The intervertebral prosthetic joint of claim 66, wherein said surrounding surfaces are substantially planar.

68. The intervertebral prosthetic joint of claim 59, wherein said articular and surrounding surfaces of said first articular component are contiguous, and wherein said first articular component is a unitary body.

69. An intervertebral prosthetic joint, comprising:
a first articular component having a bearing surface adapted to engage a first vertebra; and
a second articular component having a bearing surface adapted to engage a second vertebra,
wherein each of said first and second articular components includes a flange extending from said bearing surface and configured to penetrate a corresponding one of the first and second vertebrae, said flange defining at least one opening therethrough to permit bone growth through said flange,
wherein each of said flanges comprises (i) a leading end, extending up from said bearing surface, (ii) a trailing end, extending up from said bearing surface, and (iii) a top edge, extending between said leading and trailing ends,
wherein said top edge defines a continuous linear edge between said leading and trailing ends,
wherein each of said first and second articular components includes a pair of lateral side surfaces extending between said bearing surface and an opposite surface of said articular component, and wherein each of said lateral side surfaces defines an open channel extending in the insertion direction along the length of said lateral side surface.

70. The intervertebral prosthetic joint of claim 69, wherein said open channels extend across the entire length of said lateral side surfaces.

71. The intervertebral prosthetic joint of claim 70, wherein each of said open channels has a rectangular cross-section.

72. The intervertebral prosthetic joint of claim 71, wherein a transition between said leading end and said top edge is rounded, and a transition between said trailing end and said top edge is rounded.

73. The intervertebral prosthetic joint of claim 71, wherein said open channels are configured to engage a surgical instrument for inserting said prosthetic joint.

74. The intervertebral prosthetic joint of claim 73, wherein said open channels are aligned such that the surgical instrument holds said first and second articular components at a predetermined orientation.

75. The intervertebral prosthetic joint of claim 71, wherein said leading end comprises a first edge angled toward said trailing end relative to a normal to said bearing surface.

76. The intervertebral prosthetic joint of claim 75, wherein said leading end further comprises a second edge that is not angled toward said trailing end.

77. The intervertebral prosthetic joint of claim 69, wherein said bearing surface comprises at least one of a roughened surface and a plurality of surface projections.

\* \* \* \* \*